(12) United States Patent
Boss et al.

(10) Patent No.: US 12,025,612 B2
(45) Date of Patent: *Jul. 2, 2024

(54) BROWN ADIPOCYTE PROGENITORS IN HUMAN SKELETAL MUSCLE

(71) Applicant: Energesis Pharmaceuticals, Inc., Cambridge, MA (US)

(72) Inventors: Olivier D. Boss, Boston, MA (US); Jean-Paul Giacobino, Geneva (CH)

(73) Assignee: ENERGESIS PHARMACEUTICALS, INC., Cambridge, MA (US)

( * ) Notice: Subject to any disclaimer, the term of this patent is extended or adjusted under 35 U.S.C. 154(b) by 886 days.

This patent is subject to a terminal disclaimer.

(21) Appl. No.: 16/713,048

(22) Filed: Dec. 13, 2019

(65) Prior Publication Data

US 2020/0371089 A1 Nov. 26, 2020

Related U.S. Application Data

(60) Continuation of application No. 15/198,361, filed on Jun. 30, 2016, now abandoned, which is a division of application No. 13/875,711, filed on May 2, 2013, now Pat. No. 9,410,945, which is a continuation of application No. 12/994,590, filed as application No. PCT/US2009/003217 on May 27, 2009, now Pat. No. 8,455,204.

(60) Provisional application No. 61/071,916, filed on May 27, 2008.

(51) Int. Cl.
| G01N 33/53 | (2006.01) |
| A61K 31/4439 | (2006.01) |
| C12N 5/077 | (2010.01) |
| C12N 5/0775 | (2010.01) |
| G01N 33/50 | (2006.01) |

(52) U.S. Cl.
CPC ..... *G01N 33/5061* (2013.01); *A61K 31/4439* (2013.01); *C12N 5/0653* (2013.01); *C12N 5/0667* (2013.01); *G01N 33/5023* (2013.01); *G01N 33/5044* (2013.01); *C12N 2501/01* (2013.01); *C12N 2501/385* (2013.01); *C12N 2501/999* (2013.01); *C12N 2503/02* (2013.01); *C12N 2506/13* (2013.01); *G01N 2800/04* (2013.01); *G01N 2800/042* (2013.01)

(58) Field of Classification Search
None
See application file for complete search history.

(56) References Cited

U.S. PATENT DOCUMENTS

| 8,455,204 B2 | 6/2013 | Boss et al. |
| 9,410,945 B2 | 8/2016 | Boss et al. |
| 2004/0223901 A1 | 11/2004 | Smalley et al. |
| 2006/0017191 A1 | 1/2006 | Liang et al. |
| 2007/0054949 A1 | 3/2007 | Pershadsingh |
| 2007/0264239 A1 | 11/2007 | Huard et al. |
| 2007/0287202 A1 | 12/2007 | Maehashi et al. |
| 2008/0219957 A1 | 9/2008 | Lim et al. |
| 2010/0196249 A1 | 8/2010 | Hata et al. |
| 2011/0104133 A1 | 5/2011 | Tseng et al. |
| 2016/0303100 A1 | 10/2016 | Boss et al. |

FOREIGN PATENT DOCUMENTS

| CN | 1533504 A | 9/2004 |
| WO | 2008013863 A2 | 1/2008 |
| WO | 2009151541 A1 | 12/2009 |

OTHER PUBLICATIONS

Almind et al., "Ectopic brown adipose tissue in muscle provides a mechanism for differences in risk of metabolic syndrome in mice," Proceedings of the National Academy of Sciences USA, Feb. 13, 2007; vol. 104, No. 7, pp. 2366-2371.
Anonymous, "Workshop Materials: 2011 Workshop," Workshop Materials. Retrieved from the Internet https://secure.emmes.com/pactweb/content/workshop-materials (2012).
Boss et al., "Recruitment of Brown Adipose Tissue as a Therapy for Obesity-Associated Diseases," Frontiers in Endocrinology, 2012; vol. 3, article 14, pp. 1-6.
Cannon et al., "The biochemistry of an inefficient tissue: brown adipose tissue," Essays in Biochemistry, 1985; vol. 20, pp. 110-164.
Cannon et al., "Brown adipose tissue: function and physiological significance," Physiological Reviews, Jan. 2004; vol. 84, issue 1, pp. 277-359.
Casteilla et al., "Adipose Tissue-Derived Cells: From Physiological to Regenerative Medicine," Diabetes & Metabolism, 2006; vol. 32, No. 5, pp. 393-401.
Champigny et al., "Regulation of UCP gene expression in brown adipocytes differentiated in primary culture. Effects of a new β-adrenoreceptor agonist," Molecular and Cellular Endocrinology, Jul. 1992; vol. 86, issues 1-2, pp. 73-82.

(Continued)

*Primary Examiner* — Michael D Pak
(74) *Attorney, Agent, or Firm* — SALIWANCHIK, LLOYD & EISENSCHENK

(57) ABSTRACT

Brown adipose tissue ("BAT") progenitor cells and methods for identifying BAT progenitor cells in a population of cells are provided. Methods are also provided for inducing differentiation of BAT progenitor cells into differentiated brown adipocytes, inducing expression or increased activity levels of BAT uncoupling protein-1 ("UCP1"), and for identifying agents capable of inducing differentiation of BAT progenitor cells into brown adipocytes and/or inducing expression or increased activity levels of UCP1. Differentiated brown adipocytes and agents and methods for inducing differentiation of BAT progenitor cells can be used for treatment of or the making of medicaments for the treatment of metabolic diseases or conditions in a patient such as obesity, overweight, impaired glucose tolerance, insulin-resistance, type 2 diabetes, dyslipidemia, hypertension, cardiovascular diseases, metabolic syndrome, and the like. Differentiated brown adipocytes and agents and methods for inducing differentiation of BAT progenitor cells can be used for prevention of hypothermia.

15 Claims, 5 Drawing Sheets

Specification includes a Sequence Listing.

(56) References Cited

OTHER PUBLICATIONS

Cigolini et al., "Human Brown Adipose Cells in Culture," Short notes, Experimental Cell Research, 1985; vol. 159, pp. 261-266, Academic Press, Inc., Sweden.
Cinti, Saverio, "The adipose organ: morphological perspectives of adipose tissues," Proceedings of the Nutrition Society, 2001; vol. 60, pp. 319-328.
Cinti, Saverio, "Functional Anatomy of the 'Adipose Organ'," Cachexia and Wasting: A Modern Approach, Editors Mantovani et al., Springer, Milano publisher, 2006; Chapter 1.1, pp. 3-22.
Cipriani et al., "The Bile Acid Receptor GPBAR-1 (TGR5) Modulates Integrity of Intestinal Barrier and Immune Response to Experimental Colitis," PLOS One, 2011; vol. 6, issue 10, pp. 1-11.
Office Action issued in U.S. Appl. No. 12/994,590, dated Mar. 26, 2012.
Office Action issued in U.S. Appl. No. 12/994,590, dated Oct. 15, 2012.
Corre et al., "Human bone marrow adipocytes support complete myeloid and lymphoid differentiation from human CD34 cells," British Journal of Haematology, Nov. 2004; vol. 127, issue 3, pp. 344-347.
Cousin et al., "Occurrence of brown adipocytes in rat white adipose tissue: molecular and morphological characterization," Journal of Cell Science, 1992; vol. 103, pp. 931-942.
Crisan et al., "A Reservoir of Brown Adipocyte Progenitors in Human Skeletal Muscle," Stem Cells, 2008; vol. 26, Issue 9, pp. 2425-2433.
Cypress et al., "Identification and importance of brown adipose tissue in adult humans," New England Journal of Medicine, Apr. 9, 2009; vol. 360, No. 15, pp. 1509-1517.
Del Mar Gonzalez-Barroso et al., "The human uncoupling protein-1 gene (UCP1): present status and perspectives in obesity research," Obesity Reviews, Oct. 2000; vol. 1, issue 2, pp. 61-72.
Donnenberg, Albert D., "Adipose Derived Stem Cells: Phenotype, Function, and Clinical Targets," Retrieved from the Internet. https://secure.emmes.com/pactweb/system/files/08workshop_13_donnenberg.pdf (2008).
Elabd et al., "Human Multipotent Adipose-Derived Stem Cells Differentiate into Functional Brown Adipocytes," Stem Cells, Nov. 2009; vol. 27, issue 11, pp. 2753-2760.
Feldmann et al., "UCP1 Ablation Induces Obesity and Abolishes Diet-Induced Thermogenesis in Mice Exempt from Thermal Stress by Living at Thermoneutrality," Cell Metabolism, Feb. 4, 2009; vol. 9, issue 2, pp. 203-209.
Foellmi-Adams et al., "Induction of uncoupling protein in brown adipose tissue: Synergy between norepinephrine and pioglitazone, an insulin-sensitizing agent," Biochemical Pharmacology, Sep. 13, 1996; vol. 52, issue 5, pp. 693-701.
Fukui et al., "A new thiazolidinedione, NC-2100, which is a weak PPAR-gamma activator, exhibits potent antidiabetic effects and induces uncoupling protein 1 in white adipose tissue of KKAy obese mice," Diabetes, May 2000; vol. 49, pp. 759-767.
Garstka et al., "Import of mitochondrial transcription factor A (TFAM) into rat liver mitochondria stimulates transcription of mitochondrial DNA," Nucleic Acids Research, Sep. 1, 2003; vol. 31, No. 17, pp. 5039-5047.
Girod et al., "Genome-wide prediction of matrix attachment regions that increase gene expression in mammalian cells," Nature Methods, Aug. 5, 2007; vol. 4, issue 9, pp. 747-753.
Goglia et al., "Morphometric-stereologic analysis of brown adipocyte differentiation in adult mice," American Journal of Physiology-Cell Physiology, Apr. 1, 1992; vol. 262, issue 4, pp. C1018-C1023.
International Search Report issued in corresponding International Patent Application No. PCT/US2009/003217, dated Sep. 15, 2009.
Irie et al., "Ectopic expression of UCP1 and adipocyte in white adipose tissue," Journal of Japan Society for the Study of Obesity, 2001; vol. 7, No. 1, pp. 63-65.
Jimenez et al., "Expression of uncoupling protein-3 in subsarcolemmal and intermyofibrillar mitochondria of various mouse muscle types and its modulation by fasting," European Journal of Biochemistry, Jun. 2002; vol. 269, issue 12, pp. 2878-2884.
Kawamata et al., "A G Protein-Coupled Receptor Responsive to Bile Acids," The Journal of Biological Chemistry, 2003; vol. 278, issue 11, pp. 9435-9440.
Kazantzis et al., "PAZ6 cells constitute a representative model for human brown pre-adipocytes," Frontiers in Endocrinology, Feb. 2012; vol. 3, article 13, pp. 1-9.
Klingenspor, Martin, "Cold-induced recruitment of brown adipose tissue thermogenesis," Experimental Physiology, Jan. 1, 2003; vol. 88, issue 1, pp. 141-148.
Kopecky et al., "Expression of the mitochondrial uncoupling protein gene from the aP2 gene promoter prevents genetic obesity," Journal of Clinical Investigation, Dec. 1995; vol. 96, issue 6, pp. 2914-2923.
Lehr et al., "The control of UCP1 is dissociated from that of PGC-1α or of mitochondriogenesis as revealed by a study using β-less mouse brown adipocytes in culture," FEBS Letters, Jul. 21, 2006; vol. 580, issue 19, pp. 4661-4666.
Lowell et al., "Development of obesity in transgenic mice after genetic ablation of brown adipose tissue," Nature, Dec. 30, 1993; vol. 366, pp. 740-742.
Lowry et al., "Protein Measurement with the Folin Phenol Reagent," Journal of Biological Chemistry, Nov. 1, 1951; vol. 193, issue 1, pp. 265-275.
Mensink et al., "Improved skeletal muscle oxidative enzyme activity and restoration of PGC-1α and PPARβ/δ gene expression upon rosiglitazone treatment in obese patients with type 2 diabetes mellitus," International Journal of Obesity (Lond), Aug. 2007; vol. 31, issue 8, pp. 1302-1310.
Nedergaard et al., "PPARgamma in the Control of Brown Adipocyte Differentiation," Biochimica et Biophysica Acta (BBA)—Molecular Basis of Disease, 2005; vol. 1740, issue 2, pp. 293-304.
Pico et al., "2-methoxyestradiol, an endogenous metabolite of 17β-estradiol, inhibits adipocyte proliferation," Molecular and Cellular Biochemistry, 1998; vol. 189, pp. 1-7.
Rodriguez et al., "Adipocyte differentiation of multipotent cells established from human adipose tissue," Biochemical and Biophysical Research Communications, Mar. 5, 2004; vol. 315, issue 2, pp. 255-263.
Rodriguez et al., "Transplantation of a Multipotent Cell Population from Human Adipose Tissue Induces Dystrophin Expression in the Immunocompetent mdx Mouse," Journal of Experimental Medicine, 2005; vol. 201, No. 9, pp. 1397-1405.
Rong et al., "Adipose Mitochondrial Biogenesis Is Suppressed in db/db and High-Fat Diet-Fed Mice and Improved by Rosiglitazone," Diabetes, Jul. 2007; vol. 56, pp. 1751-1760.
Rothwell et al., "A role for brown adipose tissue in diet-induced thermogenesis," Nature, Sep. 6, 1979; vol. 281, pp. 31-35.
Russell et al., "Brown Adipocyte Progenitor Population is Modified in Obese and Diabetic Skeletal Muscle," International Journal of Obesity, 2011; vol. 36, issue 1, pp. 155-158.
Seale et al., "PRDM16 controls a brown fat/skeletal muscle switch," Nature, 2008; vol. 454, pp. 961-968.
Sengenès et al., "Preadipocytes in the Human Subcutaneous Adipose Tissue Display Distinct Features from the Adult Mesenchymal and Hematopoietic Stem Cells," Journal of Cellular Physiology, 2005; vol. 205, issue 1, pp. 114-122.
Supplementary European Search Report issued in European Application No. 09762837, dated May 30, 2012.
Tsukiyama-Kohara et al., "Adipose tissue reduction in mice lacking the translational inhibitor 4E-BP1," Nature Medicine, Oct. 2001; vol. 7, issue 10, pp. 1128-1132.
Van Marken Lichtenbelt et al., "Cold-activated brown adipose tissue in healthy men," New England Journal of Medicine, Apr. 9, 2009; vol. 360, No. 15, pp. 1500-1508.
Virtanen et al., "Functional brown adipose tissue in healthy adults," New England Journal of Medicine, Apr. 9, 2009; vol. 360, No. 15, pp. 1518-1525.
Wilson-Fritch et al., "Mitochondrial remodeling in adipose tissue associated with obesity and treatment with rosiglitazone," Journal of Clinical Investigation, Nov. 2004; vol. 114, No. 9, pp. 1281-1289.

(56) References Cited

OTHER PUBLICATIONS

Wu et al., "Transcriptional activation of adipogenesis," Current Opinion in Cell Biology, Dec. 1, 1999; vol. 11, issue 6, pp. 689-694.
Young et al., "Brown adipose tissue in the parametrial fat pad of the mouse," Federation of European Biochemical Societies, 1984; vol. 167, No. 1, pp. 10-14.
Zhou et al., "Cidea-deficient mice have lean phenotype and are resistant to obesity," Nature Genetics, Sep. 2003; vol. 35, No. 1, pp. 49-56.
Zilberfarb et al., "Human immortalized brown adipocytes express functional β3-adrenoceptor coupled to lipolysis," Journal of Cell Science, 1997; vol. 110, pp. 801-807.
Balint, B. L. et al. "Selective Modulators of PPAR Activity as New Therapeutic Tools in Metabolic Diseases" *Endocrine, Metabolic & Immune Disorders—Drug Targets,* 2006, pp. 33-43, vol. 6, No. 1.
Hamblin, M. et al. "PPARs and the Cardiovascular System" *Antioxidants & Redox Signaling,* 2009, pp. 1415-1452, vol. 11, No. 6.

Adult muscle

☐ UCP1
■ leptin

Adult WAT

SEQUENCE LISTING

```
<160> NUMBER OF SEQ ID NOS: 29

<210> SEQ ID NO 1
<211> LENGTH: 19
<212> TYPE: DNA
<213> ORGANISM: Human

<400> SEQUENCE: 1
cctcaccgca gggaaagaa                                                   19

<210> SEQ ID NO 2
<211> LENGTH: 21
<212> TYPE: DNA
<213> ORGANISM: Human

<400> SEQUENCE: 2
ctaacgactg gaggagtggc a                                                21

<210> SEQ ID NO 3
<211> LENGTH: 22
<212> TYPE: DNA
```

<213> ORGANISM: Mouse

<400> SEQUENCE: 3
cgatgtccat gtacaccaag ga                                    22

<210> SEQ ID NO 4
<211> LENGTH: 20
<212> TYPE: DNA
<213> ORGANISM: Human

<400> SEQUENCE: 4
ttgtggcttc ttttctgcga                                       20

<210> SEQ ID NO 5
<211> LENGTH: 23
<212> TYPE: DNA
<213> ORGANISM: Human

<400> SEQUENCE: 5
ccaaaaccct catcaagaca att                                   23

<210> SEQ ID NO 6
<211> LENGTH: 21
<212> TYPE: DNA
<213> ORGANISM: Human

<400> SEQUENCE: 6
aagtcaccgg tttggacttc a                                     21

<210> SEQ ID NO 7
<211> LENGTH: 21
<212> TYPE: DNA
<213> ORGANISM: Human

<400> SEQUENCE: 7
catctgcact gccaagactg a                                     21

<210> SEQ ID NO 8
<211> LENGTH: 22
<212> TYPE: DNA
<213> ORGANISM: Human

<400> SEQUENCE: 8
gcaaagtgaa agaaggcatg aa                                    22

<210> SEQ ID NO 9
<211> LENGTH: 21
<212> TYPE: DNA
<213> ORGANISM: Mouse

<400> SEQUENCE: 9
caaatgctgg accaaacaca a                                     21

<210> SEQ ID NO 10
<211> LENGTH: 21
<212> TYPE: DNA
<213> ORGANISM: Mouse

<400> SEQUENCE: 10
ccatccagcc attcagtctt g                                     21

<210> SEQ ID NO 11
<211> LENGTH: 17

<212> TYPE: DNA
<213> ORGANISM: Human

<400> SEQUENCE: 11
tccggctcca ggtccaa                                                   17

<210> SEQ ID NO 12
<211> LENGTH: 21
<212> TYPE: DNA
<213> ORGANISM: Human

<400> SEQUENCE: 12
tgattgttcc caggacacct t                                              21

<210> SEQ ID NO 13
<211> LENGTH: 22
<212> TYPE: DNA
<213> ORGANISM: Human

<400> SEQUENCE: 13
catcactggc tatttcctga tg                                             22

<210> SEQ ID NO 14
<211> LENGTH: 21
<212> TYPE: DNA
<213> ORGANISM: Human

<400> SEQUENCE: 14
agccgaatgt gtaaaggaca g                                              21

<210> SEQ ID NO 15
<211> LENGTH: 21
<212> TYPE: DNA
<213> ORGANISM: Human

<400> SEQUENCE: 15
gtatttgcct atcccagtgc c                                              21

<210> SEQ ID NO 16
<211> LENGTH: 22
<212> TYPE: DNA
<213> ORGANISM: Human

<400> SEQUENCE: 16
catacttctt cacccactgc tc                                             22

<210> SEQ ID NO 17
<211> LENGTH: 22
<212> TYPE: DNA
<213> ORGANISM: Human

<400> SEQUENCE: 17
catgtactgc tcctgataag ac                                             22

<210> SEQ ID NO 18
<211> LENGTH: 21
<212> TYPE: DNA
<213> ORGANISM: Human

<400> SEQUENCE: 18
gcctacactt gacatgcata c                                              21

<210> SEQ ID NO 19

```
<211> LENGTH: 21
<212> TYPE: DNA
<213> ORGANISM: Human

<400> SEQUENCE: 19
aaggcaacct cagccatgtc g                                              21

<210> SEQ ID NO 20
<211> LENGTH: 21
<212> TYPE: DNA
<213> ORGANISM: Human

<400> SEQUENCE: 20
ctcgactcca cagtctggga c                                              21

<210> SEQ ID NO 21
<211> LENGTH: 18
<212> TYPE: DNA
<213> ORGANISM: Human

<400> SEQUENCE: 21
cctcgccttt gccgatcc                                                  18

<210> SEQ ID NO 22
<211> LENGTH: 20
<212> TYPE: DNA
<213> ORGANISM: Human

<400> SEQUENCE: 22
ggaatccttc tgacccatgc                                                20

<210> SEQ ID NO 23
<211> LENGTH: 42
<212> TYPE: DNA
<213> ORGANISM: Human

<400> SEQUENCE: 23
tcgtaagctt agaggcggcg gctgcagacg gagcgcggtg tt                       42

<210> SEQ ID NO 24
<211> LENGTH: 32
<212> TYPE: DNA
<213> ORGANISM: Human

<400> SEQUENCE: 24
acgaagatct cattacccca aatagcatca ca                                  32

<210> SEQ ID NO 25
<211> LENGTH: 41
<212> TYPE: DNA
<213> ORGANISM: Human

<400> SEQUENCE: 25
tcgtaagctt agaggcggcg gctgcagacg gagcgcggtg t                        41

<210> SEQ ID NO 26
<211> LENGTH: 33
<212> TYPE: DNA
<213> ORGANISM: Human

<400> SEQUENCE: 26
acgaaccggt cagaagtggt gaagccagcc tgc                                 33
```

```
<210> SEQ ID NO 27
<211> LENGTH: 36
<212> TYPE: DNA
<213> ORGANISM: Human

<400> SEQUENCE: 27
tcgtaccggt acaggctctg ggaagtagga gaaagt                                36

<210> SEQ ID NO 28
<211> LENGTH: 32
<212> TYPE: DNA
<213> ORGANISM: Human

<400> SEQUENCE: 28
acgaagatct cattacccca aatagcatca ca                                    32

<210> SEQ ID NO 29
<211> LENGTH: 6120
<212> TYPE: DNA
<213> ORGANISM: Human

<400> SEQUENCE: 29
cattacccca aatagcatca cattctatct ctggatcacc attttttacac ttatctagaa       60 tttgcccacc tgtagtttcc actcttcggc actaattatt ttgcttaatt gcgtacagaa      120
caaatctacc ccgtccactg tctatgcctt caagtatctg agaacagtaa tgtcctgttc      180
ggtaagtcat tttctccttt tcactctctg gtccttccat ggggcttcaa tccccataca      240
cctctttttt ctaaatttca taggtcagtt ttcctgtctc ttctaccagg ttctactgaa      300
gatgaaaaaa agtgcttttt taaaccaaaa gtattgcaat gtttatttta tctttgtaag      360
ttccttagta atatatacaa atcaagtaaa agatatatgt tgcatgtgat attttaactt      420
ttgatatgac ttattgaaaa aatatataag gatacatagc cattgtgtgt cttcaaatca      480
taggaaagta tcatgtcgcg aatgtattgg gaaggcagtt ggggtatcac gtagtagttg      540
agagttaggg ggtcaggcag atcctcagtg taccatttac tggttccgtg acctaggaga      600
agttatttaa cttctctgag cctctgagtt cctcatcag tgaagtggga ataacaataa       660
tatatgcctc caaaggccgc aatgaggact aactgtgtta agttttgtaa aatgcctaaa      720
atattatagt gtctggcact tgttcaatgc tatgtatttg ttaaatacat gacatgaata      780
aatctttcat tgagttatga ggattaggta catcaggtgc ttagcataaa gagtgattta      840
ttaataagaa taggctcatg atgcaggaat attcatcaca tatgtaaata atctgaagct      900
cagagaagtt aagtaatttg gccatgctta cccagtcagt tattatctta gtgagaattt      960
gaacatgggc ctcctggtct cttaatcacc atgctatacc acttatatca gcatagaaat     1020
ggatattttt ctccttaacg cagagtttga tagtctttgt ctctttgtat gggctggac      1080 taagaaaacc caatcctgtc ctctttctac tttttctctg ttcctaagag cactccctt      1140 tctctgttgt atatcagttc ctaatggtag acacttgagc accactattc tgtacagctc     1200
tccgacaatc ccacatctag atgccaagct gaggttggca ttctcactaa tttgctgtta     1260
taaatattaa gctatcataa gcgttagcct acatatgact ctttcatatg ttagttaatt     1320 atttagggt agaaatccaa aagtggagtt accagaagtg gatatagaca ttctggctgg      1380
gtgtgatggt tcatgcctgt aatcccagca ctttgggagg cagaggcagg cggatcactt     1440
gaggccagga gtttgagatc agcctgggcc aacacagcga aaccccatct ctactaaaaa     1500
ttccaaaact agccaggcat agtggcacat gcctgtactc ccagctactt gggaggctaa     1560
```

-continued

```
gacacaagaa tcgcttgaac ccgggaggga ggtggaggtt gcggtgagct gagattgtgc   1620
caccgtactc cagcctgggt gacacagcta gactctgttt caaaaaaaaa aagaaaaaga   1680
aaagaaaaaa atagactttc tcttggctca gtgtatactg ccaaattgtt ttccaaaaaa   1740
attgtgtcaa tgtataacac catcactaat atagtattga tattatggtt attacatttt   1800
aaaattcata atttgtaatt ataacattca taatttatta ctatttataa tattaatgta   1860
aatgtatatt atatataaat gttatagtaa ttataacttt ggtagtgaca aagtattaat   1920
ttattaggtg aagtatatgc ttttttatta gtgataataa atatatcctc tctcccatta   1980
taaaagtttg tatttcttct tttagaaatt gattcttctg tcatttgcac atttatctgt   2040
ataattataa cagggtattt cccagtggtg gctaatgaga gaattatggg aaagtataga   2100
acactattca aatgcaaagc actgtatgat ttttatttaa taggaagaca ttttgtgcag   2160
cgatttctga ttgaccacag tttgatcaag tgcatttgtt aatgtgttct acattttcaa   2220
aaaggaaagg agaatttgtt acattcagaa cttgctgcca ctcctttgct acgtcataaa   2280
gggtcagttg cccttgctca tactgaccta ttctttacct ctctgcttct tctttgtgcc   2340
agaagagtag aaatctgacc ctttggggat accaccctct cccctactgc tctctccaac   2400
ctgaggcaaa ctttctccta cttcccagag cctgtcagaa gtggtgaagc cagcctgctc   2460
cttggaatcc agaactactt tcagaatctt gaacttctgt gacctctcag ggtccccttg   2520
tgtgaagttt ttgacgtcag cttctcctgt gacccttaga agtcactctt gtgtctagca   2580
catcccaggt gctcagtcac cattgaacta cagtcatact atctcctggc aaaggctctt   2640
aactgtccat gttagcctga tattaatatc ctggaagctt atactgtcgt tcttccttcc   2700
aggtttaaat aaggcagccc ctttatcctg tcacaggtcc tctctcccta cctatcctta   2760
cctgttttgg ataacaacct ttcttatttc taatagattt atttatttct cacatttcct   2820
tcccttatca tagttttcct ctcactttct cctctagttt gtcatactct ggctttaaaa   2880
catgcaaaca tgtgccttat ggggaaaaaa agacaatttt aatttacctt gcttcttctt   2940
tacaaatgta ttgtggcttc ttcttatagt ccaaatctaa aactctttac ccacccactg   3000
ccttgaactc cttcctcgtt gtgaaagtag gatggggcaa agagagaatg catgcccctc   3060
ccaactgctc aaacaagtaa aggtgctgtt acagttatct tttgctacct taatacaata   3120
attattttat tatatctcac aattttatgg atcaggaatt tagactgggc tcagctaggc   3180
gattcttctg ctttactgac atcataggag atcacttggt ggtattcaac tgtcaggtag   3240
gcttatctgg agggtccaag atagctgtac tctggtgcct ggtgccttgg taaagaggga   3300
tgatgatgtg gggcctctcc agcatgaaca gcctcagaga agtttgcttt cttacatgct   3360
ggcccagggc tccaagagca aatgttgcag tgagtaaagc agaagataca aggacttttta  3420
taatctggtc tcagaagcca catggcatca gttctgtatt attctattgg tcaaaacatt   3480
cataagcctg ccagatgcaa ggggaaggca tatgtaccct catcttttga tgggaggaat   3540
gtgatggatt tgcaattatg ttttaaaact actacagaca gaaccactga gaaagattca   3600
tgggtagctt tggggtgagg actgggaatt aacctgttga tagcagaggt tcactagagt   3660
caacaaggaa taaggtctcc tcttgtacac tttagtcata ctataccaac attcttaacc   3720
actgcttagc catcagcctc acaacataac aactccatca tagttgtact ccctaagatc   3780
accaacaatg ttagagtcaa atccggtagg ttttctttg  ttttgtcct cctgacattt    3840
tttctaaaact tgcactggt cagacccaat ctttctttaa tcatattctt aaataccagt    3900
tctatcactg gatatgttac tgtttcttgt tctcactcta cctttgacaa agccattctt   3960
```

```
tccagactat aactctgggt ctgggtcccc ctatggtttg gcccttgaat tcttttccta    4020
gtcctatttg actagcccca ttttcccgtg aaaagcatgc cccttcatt gcatccatat     4080 catgactacc aaatacctcc tctatttctt cctcttttag catgttaaat gcagcttcct    4140
aagctctcta tctggatatc aacagtattc tctccaaata attctaagac tttaaaaatt   4200
ggtttaatct tcttacccct aaaatcaccc cccttaccaa ctgcctcatg acaatcattg    4260
gtactgtcac tgagcttgca acccatgttc ttaaacatag agtaatcttt gactccacat   4320
ctaatcattc ataaagctgt attgtctatc aaattaaatc tgacatttat gtgagagcac    4380
ttcatagtct gtaaagcact acacaggtga taacatgaag ctacactcat aatggatttg   4440
caggctctgc ttctcatttg gcttctacag cctcatccct caccaacttc ttgccctacc   4500
tctctctttc ttccccatca cccaatttcc cagtcagtca ggccaacaga atgcattcta   4560
tatacgcgac ttgctttccc caacatcttt gcctgtatgc atgccactta tttgcctcag   4620
ttgatcttta tttcaacaag tgtttgcaga ggagaaacct cgctggctcc ttctcctttc   4680 tattttttt cagaggctac ccgtcaggtc aacattgcct ttttcaggga agctctgcaa    4740
gcctgacctc ccttggaagt gccttaggac tggcttcttg cacagtacac aacctttact  4800
tatagagggt ttggagatta ttctttattc atgtcttatt tctcctgctc ctggaggaga   4860
tgactctgac ttccactgac tcttttgggg ggcttaagtc agggttgagt accagaggcc   4920
ctaaatagct ggacgtggat tctgtaata tcaaatccat cttttggctta actgagaggt   4980 tctgaaagct gggacctgac cttgtccatt tccctctttc tccagtttcc tattatttcc    5040
cactgttttt tttaaaagtt ttttgttttc ttaagttttc acaagaataa acattgaaaa   5100
taaaatttgc acaaagatcg aactaggaaa ggccacacaa ccaacacata ttacatcatt   5160
ataggtaagt tagcagggag atttcagacc tgggctagct ctggaaccac attttacact   5220
gttgaaaata aaagctggag tacagatgac tttcccaggt tcacagagtt ggtaagctgg   5280
agagctgcac ctggagccaa gcaacctgcc ctgtcctttc cactgcaccc tctaagaaat    5340
ctaattagaa ggaacaggtg gtatctcatt ttgtacggtg ctttagcaat gtactatttg    5400 cttctagtg tgtctattgt ctcgtttgac atcttctctc aaaaagtgat gaaacgaaac    5460 gctcttttg acaagttcag agtgctcttg gttcctgtgt gggattcttc caagtctgaa   5520
tttggtagtg ggaagagaag gaatccggag gaaggaggat gagaagttta aaggagagga   5580
aagggaagca gagaaggccg caaggtgcct gcaagatgtc tggggagttg gaggaatgga  5640
agagtgcccc gctcttcctt ctgggagagc tccagctagg cagaaccttt caccaaggct   5700
ctgatatcgt gctggtttcc gaaagcccca gccgaaggtg tgcagccaaa gggtgacaga   5760
aggtgaggca cgtgcggggg cgcgggtgct gaccgccgcg gtgcgccctc cctccgacgt    5820
gcggtgtgcg gggcgcagac aaccagcggc cggcccaggg ctttcgggga gcgaagcagg   5880
gctcccgagg caccgagcga gaatgggaat ggaggggacc cggtgctccc ggacacgccc   5940
ccggcaggtc ccacgcccgg gtcttctgag acctcgcgcg gcccagcccg ggagcggccc   6000
agctatataa gtcccagcgg aagaccggaa cgcagagggt cctgctggcg cgagggtggg   6060
taggagggga cgcggggact cggcccccaa caccgcgctc cgtctgcagc cgccgcctct   6120
```

BROWN ADIPOCYTE PROGENITORS IN HUMAN SKELETAL MUSCLE

CROSS REFERENCE TO RELATED APPLICATIONS

This application is a continuation of U.S. patent application Ser. No. 15/198,361 filed Jun. 30, 2016, which is a divisional of U.S. patent application Ser. No. 13/875,711 filed May 2, 2013, now U.S. Pat. No. 9,410,945, which is a continuation of U.S. patent application Ser. No. 12/994,590 filed Feb. 3, 2011, now U.S. Pat. No. 8,455,204, which is a U.S. national stage application of International Application No. PCT/US2009/003217 filed May 27, 2009, which claims priority to and the benefit of U.S. Provisional Patent Application No. 61/071,916, filed May 27, 2008, the contents of each of the foregoing applications are hereby incorporated by reference in their entirety.

TECHNICAL FIELD

This disclosure relates to brown adipose tissue, progenitor cells, cell differentiation, and brown adipose tissue uncoupling protein-1. The disclosure also relates to metabolic diseases such as obesity, type 2 diabetes, insulin-resistance and dyslipidemia.

INTRODUCTION

The epidemic of obesity is closely associated with increases in the prevalence of diabetes, hypertension, coronary heart diseases, cancer and other disorders. The role of white adipose tissue is to store lipids, and it is associated with obesity. The role of the brown adipose tissue ("BAT") is effectively the opposite. It is specialized in lipid combustion and the dissipation of energy as heat. Indeed, the brown adipocyte contains lots of mitochondria (in which cellular combustion occurs) and uniquely expresses BAT uncoupling protein-1 ("UCP1"). UCP1 acts as an uncoupler of oxidative phosphorylation, resulting in dissipation of energy as heat. The sympathetic nervous system stimulates mitochondriogenesis and UCP1 expression and activity. BAT-associated thermogenesis in rodents is increased upon exposure to low temperature (e.g., preventing hypothermia) or as a result of overeating, burning excess absorbed fat and preventing weight gain. BAT, by modifying susceptibility to weight gain and by consuming large amounts of glucose, also improves insulin sensitivity. It therefore plays an important role in the maintenance of body temperature, energy balance and glucose metabolism.

Experiments with transgenic animals support the potential anti-obesity properties of BAT. For example, the genetic ablation of BAT has been reported to cause obesity, while genetic increase in the amount and/or function of BAT (and/or UCP1 expression) reportedly promotes a lean and healthy phenotype. Specifically, mice with a higher amount of BAT gain less weight and are more insulin-sensitive than control mice. Recently, ectopic BAT depots were evidenced in the mouse muscle, which were proposed to provide a genetic-based mechanism of protection from weight gain and metabolic syndrome.

Although UCP1 is reported to play a role in the control of energy balance in rodents and UCP1-expressing BAT is present in human neonates, it has long been thought that there was no physiologically relevant UCP1 expression in adult humans. Indeed, UCP1-expressing BAT was thought to disappear early in life, and adult humans were thought to be devoid of BAT.

SUMMARY

Applicants have identified the presence of cells in various tissues that are capable of differentiating into brown adipocytes. In one aspect, Applicants have identified a population of such cells, which Applicants refer to as BAT progenitor cells, in skeletal muscle. The present disclosure provides methods for sorting cells from various tissues to identify and isolate BAT progenitor cells. In some embodiments, BAT progenitor cells are isolated from human skeletal muscle. Methods are provided for differentiating BAT progenitor cells in vitro and in vivo into brown adipocytes. In some embodiments, BAT progenitor cells can be caused to differentiate in vivo into brown adipocytes in a human subject.

In some embodiments, BAT progenitor cells of the present disclosure can be expanded in culture. In another aspect, differentiated BAT progenitor cell UCP1 mRNA expression is increased by agents such as cell-permeating cAMP derivatives, peroxisome-proliferator-activated receptor (PPARγ) agonists, and the like. BAT progenitor cells that have been differentiated into brown adipocytes may, in some embodiments, contain large amounts of mitochondrial transcription factor A (mtTFA) and PPARγ coactivator-1α (PGC-1α), which are both involved in the control of mitochondriogenesis, as well as of mitochondrial marker cytochrome oxidase IV (COX IV). Differentiated BAT progenitor cells can exhibit one or more of the following characteristics: high levels of UCP1 expression, high levels of uncoupled respiration, high metabolic rate. Applicants provide differentiated cells that are equipped to metabolize glucose, oxidize fatty acids, and dissipate energy as heat via uncoupling of oxidative phosphorylation.

The present disclosure provides methods for detection of UCP1 mRNA in the skeletal muscle of adult humans, and methods for increasing its expression in vivo. Although prior studies concerning UCP1 expression in adult humans have focused on white adipose tissue, applicants disclose the existence in, and isolation from, human skeletal muscle of brown adipose progenitor cells with a substantial potential for UCP1 expression. In some embodiments, this reservoir of BAT progenitor cells can be utilized for modulation of energy dissipation and for treating obesity, diabetes, and metabolic diseases.

In some aspects, this disclosure provides methods for the identification of BAT progenitor cells in human skeletal muscle and methods to isolate these cells from human skeletal muscle samples. Also provided are conditions and agents (e.g., compounds, proteins, biologicals, and the like) that promote the differentiation of these progenitor cells to brown adipocytes in vitro, in vivo, or both. Methods are provided for using these conditions and agents to treat metabolic diseases such as obesity, type 2 diabetes, insulin-resistance, dyslipidemia, and the like.

The present disclosure provides assays that allow identification of agents (e.g., compounds, proteins, biologicals, and the like) that induce the expression of the UCP1 gene, promote the differentiation of BAT progenitor cells into brown adipocytes in vitro, promote the differentiation of BAT progenitor cells to brown adipocytes in vivo, or combinations of these activities. According to some embodiments, agents identified in this manner can be used to treat metabolic diseases such as obesity, type 2 diabetes, insulin-resistance, dyslipidemia, and the like.

These and other features of the present disclosure are set forth herein.

BRIEF DESCRIPTION OF THE FIGURES

FIG. 1A scale bar is 50 µM.

FIGS. 2A-2C: Phase contrast; scale bar: 50 µm.

FIGS. 4A and 4C: Phase contrast; scale bar: 50 µm.

DESCRIPTION OF VARIOUS EMBODIMENTS

Figure 1A:
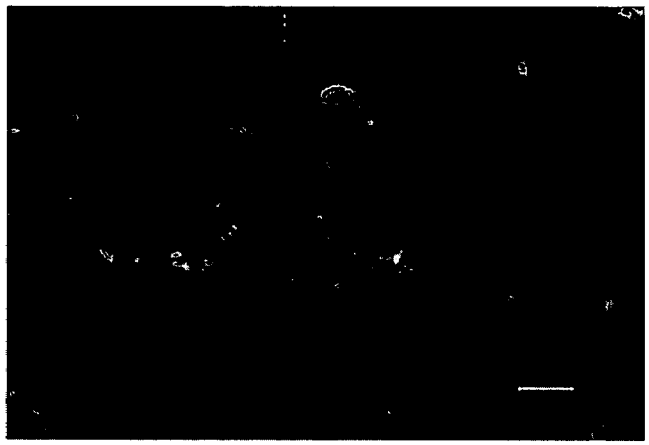
FIGS. 1A and 1B show immunohistochemical description (FIG. 1A) and FACS analysis and sorting (FIG. 1B) of vascular cells in human fetal muscle.

The present disclosure provides methods for identifying and isolating BAT progenitor cells in and from various tissues, including, in some embodiments, the identification of common brown adipocyte progenitor cells in human skeletal muscle and isolation of such cells from human skeletal muscle samples. In some embodiments, the cell sorting can be done by immunohistochemical analysis of cell surface markers such as cluster of differentiation/designation ("CD") molecules CD34, CD45, CD56, and CD146. Hematopoetic cells and myogenic progenitors can be sorted based on identification of CD45 and CD56, respectively, on their cell surfaces. CD34 and CD146 can be used to identify endothelial cells and pericytes, respectively. In one aspect, expression of CD34 identifies a cell as a progenitor of a brown adipocyte.

Flow cytometry, fluorescent-activated cell sorting ("FACS"), and other cell sorting techniques known in the art can be used for sorting cells obtained from various tissues and for separating BAT progenitor cells from other cells. Among other techniques known in the art, multi-color FACS can be used to identify CD34+ endothelial cells and CD146+ pericytes and separate them from each other and from CD45+ hematopoietic cells and CD56+ myogenic progenitors. Reverse transcriptase polymerase chain reaction ("RT-PCR") analysis can be used to confirm the absence of hematopoietic cells and myogenic progenitors from the populations of CD34+ and CD146+ cells.

Applicants have found that a population of progenitors is present in skeletal muscle, and that this population is, in some embodiments, found in skeletal muscle but not in white adipose tissue and, in some embodiments, exclusively found in skeletal muscle (i.e., not in other tissues). The skeletal muscle may be that of a human or of any animal, and populations of progenitor cells may be diffuse in the skeletal muscle or concentrated in discrete regions. BAT progenitor cells may, in some embodiments, be found between myofibers. Skeletal muscle BAT progenitor cells may be a stationary population or may be mobile both within skeletal muscle or other tissue and between and among different tissues. Further, BAT progenitor cells can be found in fetal, juvenile, and adult skeletal muscle.

The present teachings provide BAT progenitor cells isolated from various tissues. For example, BAT progenitor cells isolated from human skeletal muscle are provided. In some embodiments, the BAT progenitor cells are found in skeletal muscle but not in white adipose tissue, and/or are exclusively found in skeletal muscle. Some BAT progenitor cells may express UCP1, mitochondrial transcription factor A (mtTFA), and/or PPARγ coactivator-1α (PGC-1α) as well as one or more of the corresponding mRNAs. The present disclosure provides methods for detection of BAT progenitor cells and/or UCP1 mRNA in the skeletal muscle of adult humans. Although prior studies concerning UCP1 expression in adult humans have focused on white adipose tissue, applicants disclose the existence in, and isolation from, human skeletal muscle of brown adipose progenitor cells with a high potential for UCP1 expression. In some embodiments, a reservoir of BAT progenitor cells in skeletal muscle provides a mechanism for modulating energy dissipation for treatment of metabolic diseases such as obesity, diabetes, and the like.

At least a portion of the population of progenitor cells present in skeletal muscle is capable of differentiating into genuine brown adipocytes, and, in some embodiments, a portion of the population of progenitor cells present in skeletal muscle are capable of being differentiated in vitro into genuine brown adipocytes. The present disclosure provides methods for expanding BAT progenitor cell cultures and methods for differentiating BAT progenitor cells into genuine BAT cells, including methods for differentiating previously sorted cells in an adipogenic medium. In some embodiments, differentiation of sorted progenitor cells into brown adipocytes can be performed using conditions that sustain white adipocyte differentiation or by use of agents determined to promote differentiation of progenitors into brown adipocytes.

Some embodiments utilize the presence of UCP1, mitochondrial transcription factor A (mtTFA), and/or PPARγ coactivator-1α (PGC-1α) as well as one or more of the corresponding mRNAs, to identify BAT progenitor cells that have begun to at least partially differentiate. High metabolic rate or high levels of uncoupled respiration, glucose utilization, fatty acid oxidation, or combinations of the foregoing characteristics with each other or other characteristics, can be used to identify BAT progenitor cells that have begun to at least partially differentiate. For purposes of this disclosure, BAT progenitor cells that have begun to at least partially differentiate into brown adipocytes are referred to as "differentiated brown adipocytes."

As an example, cells determined to express the CD34 marker (i.e., CD34+ cells) can be differentiated into brown adipocytes by culturing in DMEM-Ham's F-12 medium containing 0.86 µM insulin, 10 µg/ml transferrin, 0.2 nM triiodothyronine, 1 µM rosiglitazone, 100 µM 3-isobutyl-1-methylxanthine, 1 µM dexamethasone and 1% penicillin-streptomycin. Other agents may also be used to promote differentiation of progenitor cells into brown adipocytes. In some embodiments, agents identified according to the teachings of this disclosure are used to promote differentiation of progenitor cells into brown adipocytes. In some embodiments, differentiated brown adipocytes exhibit high levels of UCP1 expression, high levels of uncoupled respiration, and/or high metabolic rate.

The present disclosure provides methods for increasing UCP1 mRNA expression in BAT progenitor cells, differentiated brown adipocytes, or both. For example, agents such as cell-permeating cAMP derivatives and peroxisome-proliferator-activated receptor-γ (PPAR-γ) agonists can be used to increase UCP1 mRNA expression in BAT progenitor cells, differentiated brown adipocytes, or both. Enhanced UCP1 expression can be determined by methods known in the art, including measurement of UCP1 mRNA by quantitative RT-PCR. Exemplary primers for use in RT-PCR analysis of UCP1 mRNA are provided as SEQ ID NOS: 1-4 and 11-12.

BAT progenitor cells exposed to adipogenic media can contain higher levels of UCP1 mRNA than BAT progenitor cells that are not exposed to adipogenic media. Cyclophilin mRNA levels can serve as a normalizing value (reflecting the number of cells or the total amount of RNA) for evaluating the abundance of UCP1 mRNA in a cell. In some embodiments, UCP1 mRNA levels in BAT progenitor cells not exposed to adipogenic media are not detectable using RT-PCR while UCP1 mRNA levels in differentiated brown adipocytes is detectable and can be normalized to cyclophilin mRNA levels. As a comparative measure of UCP1 expression, UCP1 mRNA levels in differentiated brown adipocytes can be compared to UCP1 mRNA levels in cultured mouse brown adipocytes. The present disclosure provides UCP1 mRNA levels in differentiated brown adipocytes of about 25% of the UCP1 mRNA levels in cultured mouse brown adipocytes, while in other embodiments the UCP1 mRNA level is about 25±10% or from about 15% to about 30% of the UCP1 mRNA levels in cultured mouse brown adipocytes. The present disclosure contemplates UCP1 mRNA levels in differentiated brown adipocytes in a range of from about 5% to about 100% of the UCP1 mRNA levels in cultured mouse brown adipocytes. In some embodiments, the UCP1 mRNA levels can be in excess of 100% of the UCP1 mRNA levels in cultured mouse brown adipocytes.

Differentiated brown adipocytes can contain significantly higher levels of UCP1 mRNA than cells in same-species or same-individual adult skeletal muscle biopsies. In addition, the quantity of UCP1 protein in a differentiated brown adipocyte can be approximately equal to the quantity of UCP1 protein in same-species or same-individual fetal BAT. The present disclosure contemplates UCP1 mRNA levels in human differentiated brown adipocytes being approximately equivalent to UCP1 mRNA levels in human brown adipocytes in vivo. In some embodiments the UCP1 mRNA level in a human differentiated brown adipocyte can be in a range from about 1% to many times greater than UCP1 mRNA levels in human brown adipocytes in vivo.

The present disclosure provides methods for increasing UCP1 mRNA levels in BAT progenitor cells, differentiated brown adipocytes, or both. In some embodiments, the methods provide for selectively increasing UCP1 mRNA levels in BAT progenitor cells, differentiated brown adipocytes, or both. PPARγ agonists can stimulate UCP1 mRNA production in both skeletal muscle and differentiated brown adipocytes. For example, in some embodiments, the PPARγ agonist rosiglitazone selectively stimulates UCP1 mRNA production in skeletal muscle or in differentiated brown adipocytes. Cell-permeating cAMP derivatives can stimulate UCP1 mRNA production in both skeletal muscle and in differentiated brown adipocytes. For example, in some embodiments the cell-permeating cAMP derivative 8-bromo-cAMP selectively stimulates UCP1 mRNA production in skeletal muscle or in differentiated brown adipocytes while in some embodiments the cell-permeating cAMP derivative (4-chlorophenylthio)-cAMP selectively stimulates UCP1 mRNA production in skeletal muscle or in differentiated brown adipocytes.

Mitochondrial transcription factor A ("mtTFA") and peroxisome-proliferator-activated receptor-γ coactivator-1α ("PGC-1α") are involved in the control of mitochondriogenesis. Differentiated brown adipocytes can contain large amounts of mtTFA, PGC-1α, or both. The present disclosure provides differentiated brown adipocytes having significantly increased levels of mtTFA mRNA, PGC-1α mRNA, or both, as compared to undifferentiated BAT progenitor cells. Mitochondrial marker cytochrome oxidase IV (COX IV) is involved with the mitochondrial respiratory chain. The present disclosure provides differentiated brown adipocytes having significantly increased levels of COX IV mRNA as compared to undifferentiated BAT progenitor cells.

Differentiated brown adipocytes according to some embodiments have high levels of uncoupled respiration and/or high metabolic rate. Uncoupled respiration can occur when protons leak across the inner mitochondrial membrane rather than passing through the adenosine triphosphate synthase ("ATP Synthase") enzyme to drive production of adenosine triphosphate ("ATP"). The energy released by the proton movement in the electrochemical proton gradient across the membrane is dissipated as heat, rather than in the process of making ATP. Uncoupled respiration can be measured as a function of the portion of cellular respiration (e.g., oxygen consumption) that occurs independently of ATP formation by ATP Synthase. For example, oxygen consumption in the electron transport chain of oxidative phosphorylation in the presence of oligomycin, which blocks the function of ATP Synthase, provides a measure of uncoupled respiration.

The present disclosure provides differentiated brown adipocytes having significantly increased levels of uncoupled respiration as compared to undifferentiated BAT progenitor cells. In some embodiments, the present disclosure provides differentiated brown adipocytes having levels of uncoupled respiration of about 50% of total respiration. Some embodiments exhibit uncoupled respiration at levels in a range of from about 20% to about 50% of total respiration. Using the level of uncoupled respiration in adult white adipocytes as a standard for comparison, some embodiments exhibit uncoupled respiration in a range of from about 1.5 to about 3.5 times greater than in adult white adipocytes. In some embodiments, the level of uncoupled respiration is about 2.5 times greater than in adult white adipocytes. The present disclosure provides, among other things, differentiated brown adipocytes that are equipped to metabolize glucose, oxidize fatty acids, and dissipate energy as heat via uncoupling of oxidative phosphorylation.

The present disclosure provides conditions and agents (e.g., compounds, proteins, biologicals, and the like) that promote the differentiation of BAT progenitor cells to brown adipocytes, both in vitro and in vivo. In some embodiments, the differentiation-promoting agent is: a PPARγ activator, modulator, or inhibitor (e.g., rosiglitazone), a PPARα activator or modulator (e.g., GW9578), a PPARδ activator or modulator (e.g., GW501516 or GW0742), a dual PPARα and PPARδ activator or modulator, a pan-PPAR (α, β, γ) activator or modulator (e.g., GW4148), a phosphodiesterase 4 (PDE4) inhibitor (e.g., rolipram or IBMX), a PDE7 phosphodiesterase 7 (PDE7) inhibitor (e.g., BMS 586353 or BRE 50481 or IBMX), a nuclear receptor interacting protein 1 (NRIP1) inhibitor, a phosphatidylinositol 3,4,5-trisphosphate 3-phosphatase and dual-specificity protein phosphatase (PTEN) inhibitor (e.g., potassium bisperoxo (bipyridine) oxovanadate or dipotassium bisperoxo (5-hydroxypyridine-2-carboxyl) oxovanadate), an $\alpha_1$-adrenergic full or partial agonist (e.g., phenylephrine or cirazoline), a retinoid X receptor $\alpha$ (RXR$\alpha$) activator or modulator (e.g., LGD1069 (Targretin) or 9-cis retinoic acid), a PGC-1$\alpha$ activator, a PGC-1$\beta$ inhibitor or activator, adiponectin or an activator of adiponectin receptor AdipoR1 and/or AdipoR2, a nitric oxide synthase (NOS) inhibitor or activator (e.g., 2-Ethyl-2-thiopseudourea or NG-nitro-L-arginine methyl ester (L-NAME) or adenosine), a Rho kinase-ROCK inhibitor (e.g., fasudil), brain derived neurotrophic factor (BDNF), a monoamine oxidase (MAO) A inhibitor and/or a MAO B inhibitor (e.g., isocarboxazid, moclobemide, selegiline), an activator of Proto-oncogene tyrosine-protein kinase Src (SRC), an inhibitor of an epidermal growth factor receptor (EGFR) (e.g., erlotinib or ZD1839-gefinitib or Argos protein), an inhibitor of fatty acid amide hydrolase (FAAH) (e.g., URB597), an inhibitor of mitogen-activated protein kinase (MAPK) 1 (e.g., PD98059) or 2 (e.g., PD98059) or 4 or 5 or 7 or 8 (e.g., PD98059), an inhibitor of CDK9 (e.g., 1,5,6,7-Tetrahydro-2-(4-pyridinyl)-4H-pyrrolo[3,2-c]pyridin-4-one hydrochloride), a TGR5 agonist (e.g., oleanolic acid), a 5' AMP-activated protein kinase (AMPK) activator (e.g., AICAR), bone morphogenetic protein 7 (BMP-7), a mammalian target of rapamycin (mTOR) inhibitor (e.g., rapamycin), an adenylate cyclase activator (e.g., forskolin), combinations of any of the foregoing.

In some embodiments, treatment of a subject, including a human subject, with rosiglitazone results in an increase in the production of UCP1 mRNA in the subject's skeletal muscle. Treatment of subjects with rosiglitazone can, in some embodiments, induce the appearance or differentiation of brown adipocytes in skeletal muscle, enhance expression of the UCP1 gene in existing brown adipocytes in skeletal muscle, or both. For example, in some embodiments the appearance or differentiation of brown adipocytes in skeletal muscle can be induced in a subject suffering from a metabolic disease. The brown adipocytes can provide a glucose sink with high mitochondrial and cellular respiration and fatty acid oxidation rates, dissipating energy as heat (uncoupled oxidative phosphorylation). The subject metabolic rate can be enhanced, and a decrease in body weight can be induced. Induction of the appearance or differentiation of brown adipocytes can also yield improvements in insulin sensitivity, blood glucose homeostasis and cardiovascular disease risk factors.

The present disclosure also provides assays that allow the identification of agents (e.g., compounds, proteins, biologicals, and the like) that promote the differentiation of BAT progenitor cells into brown adipocytes and/or induce the expression of the UCP1 gene in vitro, in vivo, or both. Such agents can be identified by screening compounds, proteins, biologicals, and the like. For example, in some embodiments isolated CD34+ cells can be used to screen agents for the ability to induce expression of the UCP1 gene and/or differentiation of the CD34+ cells into brown adipocytes. Agents identified in this manner can be used for a variety of research, diagnostic and therapeutic purposes, including, for example, treatment of metabolic diseases such as obesity, type 2 diabetes, insulin-resistance, dyslipidemia, and the like. In some embodiments, an agent identified by an assay according to the present disclosure is optimized for improvement of its physico-chemical and/or pharmacokinetics properties.

Expression of UCP1, mtTFA, PGC-1$\alpha$, and/or COX IV in BAT progenitor cells in vitro and in vivo can be enhanced according to methods provided in the present disclosure. In some embodiments, exposure to adipogenic media can be used to stimulate increased expression of UCP1, mtTFA, PGC-1$\alpha$, and/or COX IV in BAT progenitor cells. Agents such as a PPAR$\gamma$ activator, modulator or inhibitor (e.g., rosiglitazone), a PPAR$\alpha$ activator or modulator (e.g., GW9578), a PPAR$\delta$ activator or modulator (e.g., GW501516 or GW0742), a dual PPAR$\alpha$ and PPAR$\delta$ activator or modulator, a pan-PPAR ($\alpha$, $\beta$, $\gamma$) activator or modulator (e.g., GW4148), a PDE4 inhibitor (e.g., rolipram or IBMX), a PDE7 inhibitor (e.g., BMS 586353 or BRL 50481 or IBMX), a NRIP1 (RIP140) inhibitor, a PTEN inhibitor (e.g., potassium bisperoxo (bipyridine) oxovanadate or dipotassium bisperoxo (5-hydroxypyridine-2-carboxyl) oxovanadate), an a1-adrenergic full or partial agonist (e.g., phenylephrine or cirazoline), an RXR$\alpha$ activator or modulator (e.g., LGD1069 (Targretin) or 9-cis retinoic acid), a PGC-1$\alpha$ activator, a PGC-1$\beta$ inhibitor or activator, adiponectin or an activator of adiponectin receptor AdipoR1 and/or AdipoR2, an NOS inhibitor or activator (e.g., 2-Ethyl-2-thiopseudourea or NG-nitro-L-arginine methyl ester (L-NAME) or adenosine), a Rho kinase-ROCK inhibitor (e.g., fasudil), BDNF, a monoamine oxidase (MAO) A inhibitor and/or a MAO B inhibitor (e.g., isocarboxazid, moclobemide, selegiline), an activator of SRC, an inhibitor of EGFR (e.g., erlotinib or ZD1839-gefinitib or Argos protein), an inhibitor of FAAH (e.g., URB597), an inhibitor of MAPK 1 (e.g., PD98059), or 2 (e.g., PD98059) or 4 or 5 or 7 or 8 (e.g., PD98059), an inhibitor of CDK9 (e.g., 1,5,6,7-Tetrahydro-2-(4-pyridinyl)-4H-pyrrolo[3,2-c]pyridin-4-one hydrochloride), a TGR5 agonist (e.g., oleanolic acid), an AMPK activator (e.g., AICAR), BMP-7, an mTOR inhibitor (e.g., rapamycin), an adenylate cyclase activator (e.g., forskolin) or combinations thereof can also be used to stimulate increased expression of UCP1, mtTFA, PGC-1$\alpha$, and/or COX IV in BAT progenitor cells.

EXAMPLES

Aspects of the present teachings may be further understood in light of the following examples, which should not be construed as limiting the scope of the present teachings in any way.

Example 1: Sorting and Differentiation of Muscle Vascular Cells

In fetal skeletal muscle, CD34 and CD146 were found, by immunohistochemistry, to be expressed at the surface of endothelial cells and pericytes, respectively, although CD34 was also expressed by cells scattered in the inter-myofibrillar space. FIG. 1A shows a small vessel longitudinal section in which CD146+ pericytes (green) surround CD34+ endothelial cells (red). A similar distribution of CD34+ and CD146+ cells was observed in adult skeletal muscle.

Vascular cells from seven independent fetal muscles (16-24 weeks of gestation) were sorted using multi-color fluorescence-activated cell sorting (FACS). Hematopoietic (CD45+) cells were first gated out, as were myogenic progenitors (CD56+). Then, endothelial cells (CD34+/CD146−) and pericytes (CD34−/CD146+) were sorted. The CD34+/CD146−/CD45−/CD56− are designated thereafter as CD34+ cells and the CD34−/CD146+/CD45−/CD56− as CD146+ cells. FIG. 1B shows CD34+/CD146− and CD34−/CD146+ cell purification. Dissociated cells were stained with PE-anti-CD34, FITC-anti-CD146, PE-Cy7-anti-CD56 and APC-Cy7-anti-CD45 antibodies and run on a FACS Aria cell sorter. Following exclusion of CD45+ and CD56+ cells (left panels), cells inside the CD34+ or CD146+ gates were isolated. The CD34+ cells amounted to 8±1% of the starting fetal muscle cell population.

Figure 1C:
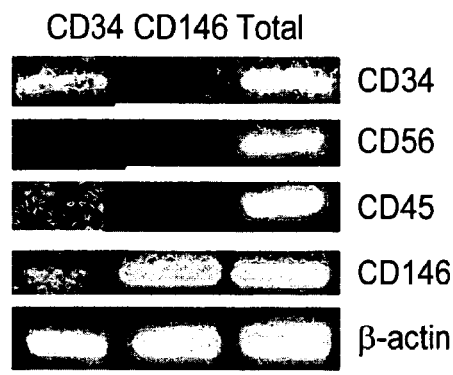
FIG. 1C shows RT-PCR analysis.
Figure 1B:
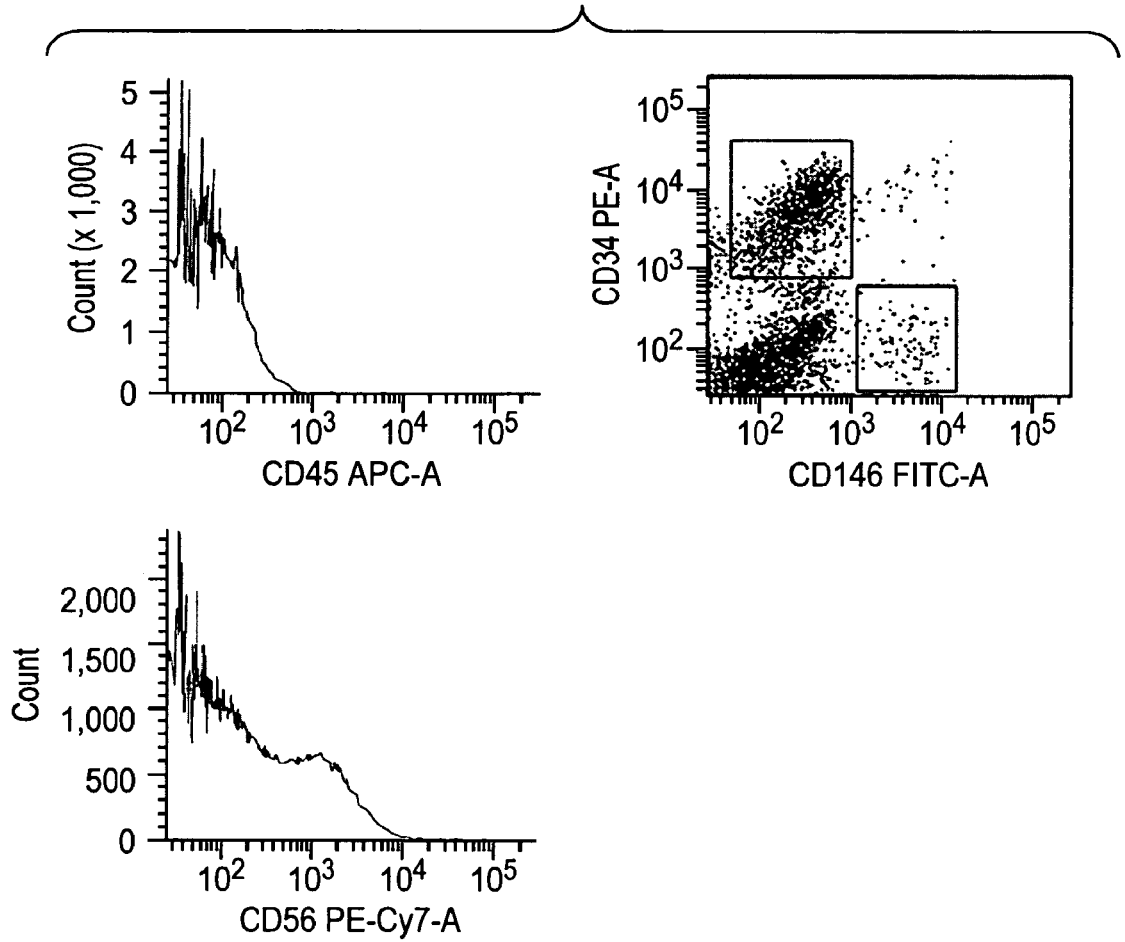

FIG. 1C shows RT-PCR analysis on CD34+/CD146−/CD45−CD56− (CD34), CD34−CD146+/CD45−/CD56− (CD146) and total non-sorted cells. Actin mRNA was measured as a control. The CD34+ cells were shown not to be contaminated by detectable CD45+ hematopoietic or CD56+ myogenic cells.

Figure 2A:
FIGS. 2A-2F show culture under adipogenic conditions of cells sorted from human fetal muscle (FIGS. 2A-2D) and RT-PCR (FIG. 2E) and Western blot (FIG. 2F) analysis for the CD34+ cells.
Figure 2B:
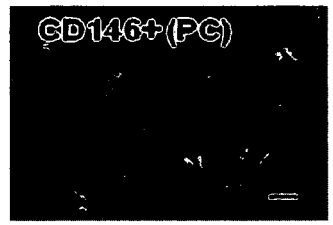
Figure 2C:
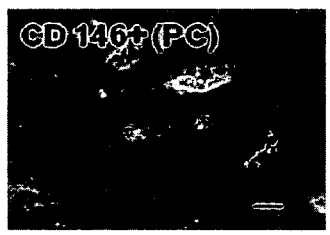
Figure 2D:

Sorted cells were grown 4-6 days in EGM2 medium and 8-12 days in the adipogenic medium described under Materials and Methods. These conditions sustain white adipocyte differentiation in WAT primary cultures. FIGS. 2A-2D show CD34+(FIG. 2A) and CD146+(FIG. 2B, FIG. 2C) cells in primary cultures (PC) and CD34+(FIG. 2D) cells expanded in culture up to passage 3 (P3). Virtually all sorted fetal muscle CD34+ cells differentiated into adipocyte-like multilocular cells (FIGS. 2A and 2D). It is noteworthy that in cell culture, the multilocular structure is shared by white and brown adipocytes. In contrast, fetal muscle CD146+ cells grew very slowly under the conditions described above. They did not reach cell confluence and displayed a pericyte-like appearance characterized by a large size, spread out shape and irregular borders (FIGS. 2B and 2C). Occasional multilocular cells could be detected (FIG. 2C) The morphology of CD34+ cells expanded in culture for up to 3 passages (4 weeks) under the conditions described above was similar to that observed in primary culture, although the size of mature adipocytes was smaller (FIG. 2D).

Example 2: UCP1 Expression in Cultivated CD34+ Cells

Figure 2E:
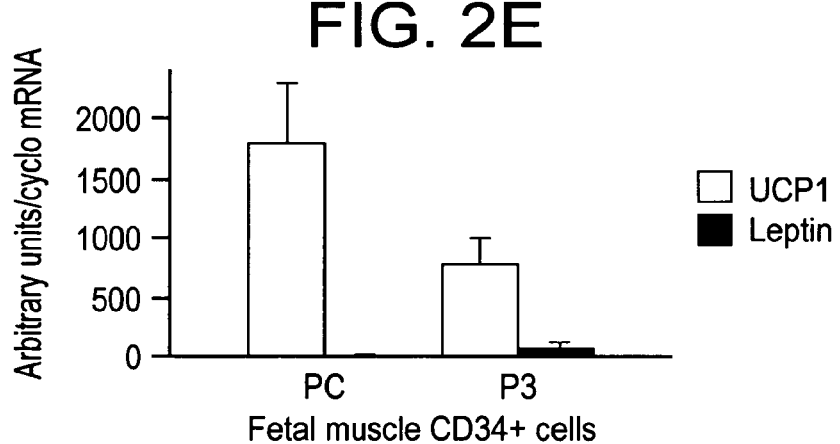

The remarkable adipocyte-like differentiation of fetal muscle CD34+ cells was an incentive for further characterization. Strikingly, quantitative RT-PCR revealed a high level of UCP1 mRNA in these cells. FIG. 2E shows quantitative RT-PCR determination of UCP1 (empty columns) and leptin (gray columns) mRNA expression in CD34+ cells in primary culture (PC) or expanded up to passage 3 (P3). The mean UCP1 mRNA level normalized to cyclophilin A was 1797±510 arbitrary units (i.e., ±s.e.m. of arbitrary values normalized using the corresponding cyclophilin A values; n=4-7), corresponding to a cycle threshold (Ct) of 22 for 25 ng of cDNA in the assay.

For comparison, the mean UCP1 mRNA level normalized to cyclophilin A in mouse brown adipocytes differentiated in culture was 7715±2649 (n=10) arbitrary units. Therefore, the level of UCP1 mRNA in human CD34+ cells amounted to almost one fourth of that in mouse brown adipocytes in culture. Human fetus BAT was not be used as a positive control for quantitative RT-PCR analysis because the risk of RNA degradation was high due to the time elapsed after the termination of the pregnancy. The amplicon was cloned and sequenced and found to be 100% identical to human UCP1. In fetal muscle CD34+ cells expanded up to passage 3 a high UCP1 mRNA expression, amounting to 43% of that detected in primary cultured cells, was still observed. UCP1 mRNA expression was not detected in non-differentiated fetal muscle CD34+ cells or in CD146+ cells in primary culture. The level of leptin mRNA was 9.95.5 and 71±52 arbitrary units in primary cultured and expanded cells, respectively (FIG. 2E).

Example 3: Additional Phenotyping of the CD34+ Cells

To better characterize the gene expression pattern of the fetal muscle CD34+ cells expanded in culture a gene chip analysis was performed. The levels of expression of several representative gene mRNAs with significant Detection P-Values (p<0.01) are shown in Table 1 and compared with those in human muscle biopsies. The following protein mRNAs were chosen: UCP1 as a reference gene, mitochondrial transcription factor A (mtTFA) and peroxisome-proliferator-activated receptor (PPARγ) and PPARγ coactivator-1α (PGC-1α), which are involved in the control of thermogenesis and mitochondriogenesis, enzymes of mitochondrial respiratory chain succinate dehydrogenase (SDH) and cytochrome oxidase IV (COX IV), enzymes of the fatty acid degradation pathway, carnitine palmitoyltransferase 1B (CPT1B), acyl-CoenzymeA dehydrogenases long chain (ACAD) and C4 to C-12 straight chain (ACADM), and the skeletal muscle markers myogenin, myogenic factor 5 (Myf5) and myogenic differentiation1 (MyoD1). Cidea, which is highly expressed in BAT and may act as a suppressor of UCP1 activity [16], was chosen as a BAT marker. The Genbank accession numbers of these genes are shown in the supplemental data.

TABLE 1

| mRNA | Accession No. | CD34 + cells | Human muscle biopsies |
|---|---|---|---|
| UCP1 | NM_021833 | 94 | n.s. |
| mTFA | NM_003201.1 | 413 | 205 |
| PPARγ | NM_138712.2 | 3326 | 84 |
| PGC-1α | NM_013261.2 | 137 | 619 |
| COX IV | NM_001861.2 | 13'082 | 13'407 |
| SDH | NM_003000.1 | 2390 | 5187 |
| CPT1B | NM_004377.2 | 99 | 639 |
| ACAD | NM_032169.3 | 1037 | 141 |
| ACADM | NM_000016.2 | 599 | 1640 |
| Myogenin | NM_002479.3 | n.s. | 267 |
| Myf5 | NM_05593 | n.s. | 21 |
| MyoD1 | NM_002478 | n.s. | 12 |
| Cidea | NM_198289.1 | 337 | n.s. |

The data in Table 1 are expressed as the average Illumina signal. The Detection P-Values are <0.01. The following abbreviations are used: n.s., not significant; mtTFA, mitochondrial transcription factor A; PPARα, peroxisome-proliferator-activated receptor-γ; PGC-1α, PPARγ coactivator-1α; COX IV, cytochrome oxidase IV; SDH, succinate dehydrogenase; CPT1B, carnitine palmitoyltransferase 1B; ACAD, acyl-CoenzymeA dehydrogenases long chain; ACADM, C-4 to C-12 straight chain; Myf5, myogenic factor 5; MyoD1, myogenic differentiation 1.

UCP1 was significantly expressed in fetal muscle-expanded CD34+ cells but not in adult muscle biopsies (for which p=0.12). The levels of mRNA expression of the selected genes in expanded CD34+ cells from fetal muscle were comparable with those of the adult muscle biopsies with the exceptions of PGC-1α and CPT1B mRNAs (which were about 5-fold less expressed in the cells) and of the PPARγ and ACAD mRNAs (which were 40- and 7-fold less expressed, respectively in the muscle biopsies). The muscle markers myogenin, Myf5 and MyoD1 mRNA were significantly expressed in the muscle but not in the cells whereas the BAT marker Cidea mRNA was expressed in the cells but not in the muscle. No $3-adrenoceptor mRNA could be detected in the gene chip analysis. It is noteworthy, however, that $β_3$-adrenoceptor mRNA was detected by quantitative RT-PCR (arbitrary value 0.084±0.044 with cyclophilin A as a reference; n=4) in fetal muscle CD34+ cells in primary culture. Measurements of mtTFA, PGC1-α and COX IV were also performed by quantitative RT-PCR to confirm the gene chip data with a different technique. The results were confirmatory, showing that fetal muscle CD34+ cells in primary culture express high levels of mtTFA, PGC1-α and COX IV mRNA [amounting to 306±117, 385±294, and 23,400±10,300 arbitrary units (n=3-4), respectively], using cyclophilin A as a reference.

Figure 2F:
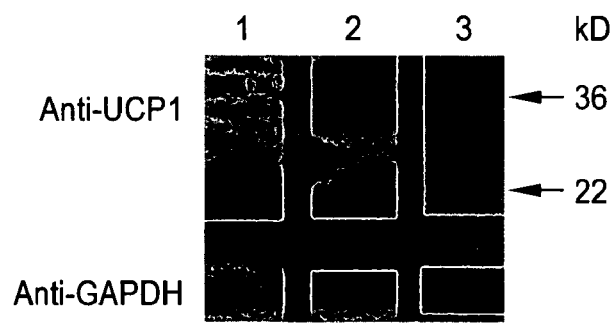

The UCP1 protein, as assessed by Western blotting with an anti-mouse antibody cross-reacting with human UCP1 (80% identity), was as abundant in primary cultured fetal muscle CD34+ cells as in fetal BAT. FIG. 2F shows representative Western blot analysis of UCP1 and glyceraldehyde phosphate dehydrogenase (GAPDH) proteins in tissue or whole cell extracts. Interscapular BAT of a 19-week fetus (Lane 1), CD34+ cells in primary culture (Lane 2), and skeletal muscle of an adult human (Lane 3) are shown. 25 μg of protein was loaded into each lane.

Example 4: Uncoupling of Oxidative Phosphorylation

To get insight into the possible function of UCP in muscle-derived cells, mitochondrial respiration of isolated cultured human fetal muscle CD34+ cells and human adult white adipocytes was compared. Basal respiration was defined as the antimycin A-sensitive oxygen consumption. Uncoupled respiration (proton leak) was defined as the percentage of basal respiration insensitive to the ATP synthase blocker oligomycin.

Figure 3A:
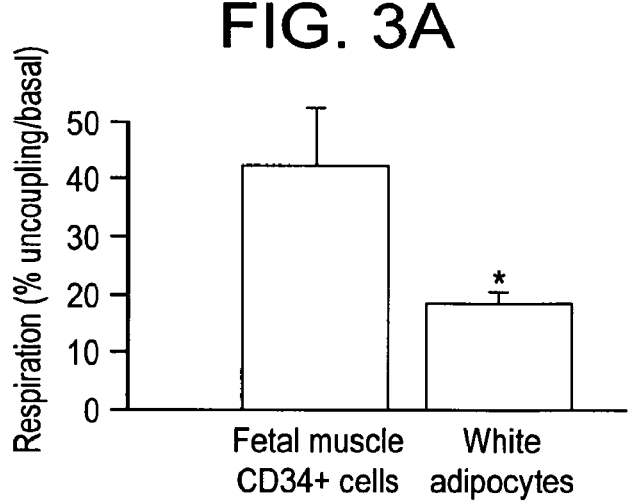
FIGS. 3A-3C show uncoupling of mitochondrial respiration (FIG. 3A) and control of UCP1 mRNA expression (FIGS. 3B and 3C) in human fetal muscle CD34+ cells.

FIG. 3A shows uncoupling of mitochondrial respiration in isolated fetal muscle CD34+ cells and in human adult white adipocytes grown in primary culture and freshly trypsinized. The results are means±s.e.m; $*p<0.05$, n=3. The ratios of uncoupled to total respiration were 47±12% and 19±2% in human fetal muscle CD34+ cells and adult white adipocytes, respectively.

Example 5: Modulation of UCP1 Expression in Cultured CD34+ Cells

Figure 3B:
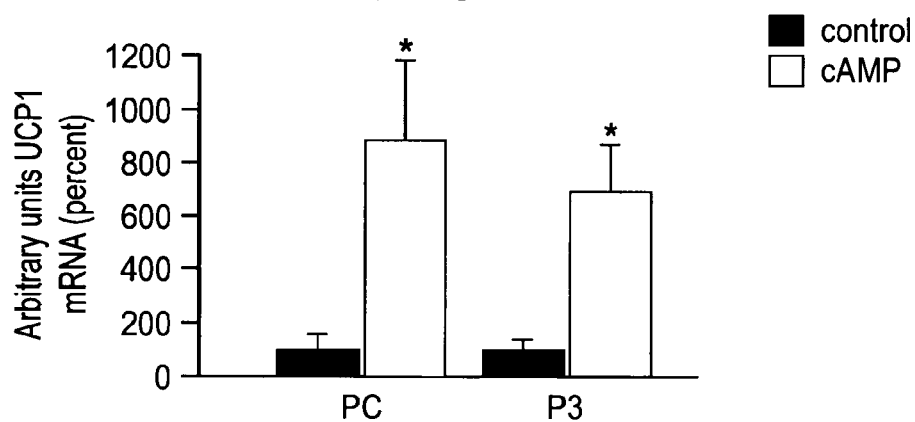

UCP1 mRNA expression in fetal muscle CD34+ cells could be modulated by drug treatment. Cell-permeating cAMP derivatives strongly stimulated (7 to 8-fold) UCP1 mRNA expression in both primary cultured and expanded cells. The effects of cAMP derivatives, 8-bromo-cAMP, 0.25 mM or (4-chlorophenylthio)-cAMP, 0.25 mM (cAMP) on UCP1 mRNA expression in CD34+ cells in primary culture (PC) or expanded up to passage 3 (P3) are shown in FIG. 3B. All the cells were grown for 4-6 days in EGM2 medium and then placed for 8-12 days in the adipogenic medium described under Materials and Methods. The results are means±s.e.m. of arbitrary values normalized using the corresponding cyclophilin A values. They are expressed in % of their respective untreated (control) values considered as 100% ($*p<0.05$, n=3-6).

Figure 3C:
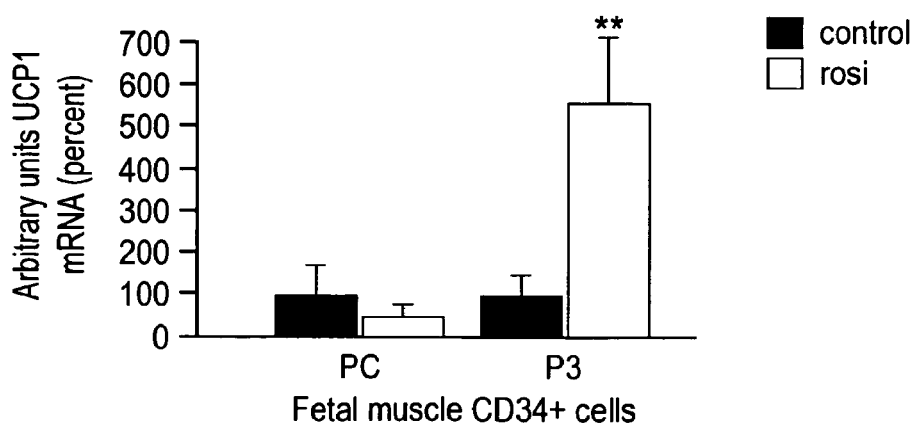

Rosiglitazone, a PPARγ agonist, had no effect in primary culture cells but strongly stimulated (8-fold) UCP1 mRNA expression in expanded cells. The effects of rosiglitazone (Rosi) 1 μM on UCP1 mRNA expression in CD34+ cell PC or P3 are shown in FIG. 3C. The results are expressed as in FIG. 3B ($**p<0.01$, n=4-7).

Example 6: Muscle Specificity and Persistence Throughout Life of Human Brown Adipocyte Progenitors The derivation of UCP1-expressing cells from human fetal muscle raised the question of the restriction of brown adipocyte progenitors to this tissue and to the fetal stage. To address this issue, CD34+ cells purified by FACS from human fetal pancreas, lung and liver were cultured under the same adipogenic conditions as fetal muscle CD34+ cells. The sorted cells grew slowly and only a small proportion of them became multilocular. UCP1 mRNA was not expressed in pancreas or lung cells; however, a minor expression was measured in liver cells, which amounted to 2% of that detected in fetal muscle CD34+ cells (not shown).

Figure 4A:
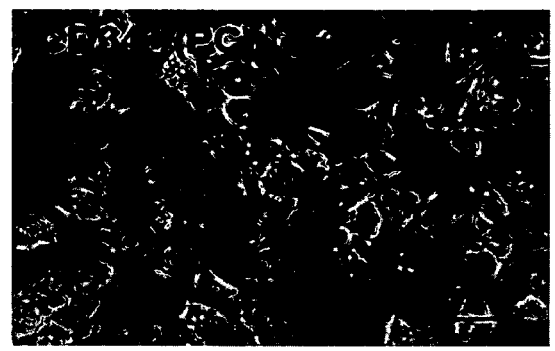
FIGS. 4A-4C show characterization of adult muscle (FIGS. 4A and 4B) and WAT cells (FIG. 4C) in adipogenic culture.
Figure 4B:
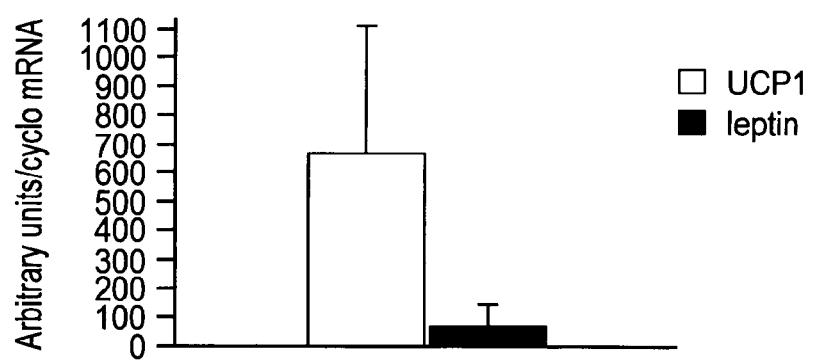
Figure 4C:
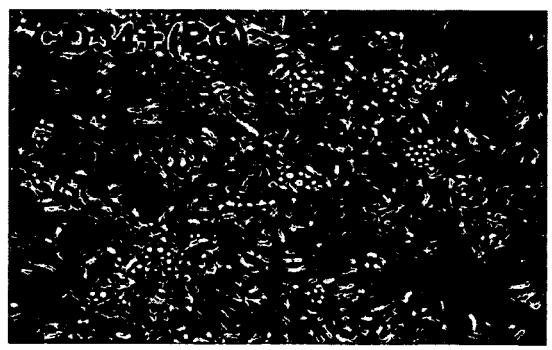

CD34+ cells sorted from 4 adult (50-78 years) human skeletal muscle samples, grown in primary culture (PC) under adipogenic conditions, also differentiated into multilocular cells. These cells were interspersed with other types of cells, some of them containing small lipid droplets (FIG. 4A). The level of UCP1 mRNA (370±132 arbitrary units) was 21% of that detected in primary cultured fetal muscle CD34+ cells. In contrast, leptin expression (7569 arbitrary units) was 7.6-fold higher than in fetal cells. FIG. 4B shows quantitative RT-PCR determination of UCP1 (empty column) and leptin (gray column) mRNA expression. All the cells were grown for 4-6 days in EGM2 medium and then placed for 8-12 days in the adipogenic medium described under Materials and Methods. The results are the means±s.e.m. of arbitrary values normalized to the corresponding cyclophilin A values (n=4-5). CD34+ cells sorted from 4 adult (45-55 years) human WAT samples were also grown in primary culture (PC) under adipogenic conditions. They became partially multilocular (FIG. 4C), but did not express UCP1 mRNA.

Example 7: Detection of UCP1 mRNA Expression in Human Muscle and Effect of Rosiglitazone In Vivo Brown adipocyte progenitors of adult human skeletal muscle can differentiate in vivo and give rise to UCP1 expressing cells. The presence of UCP1 mRNA in the adult human skeletal muscle was tracked using a high sensitivity RT-PCR technique and, in fact, low levels of UCP1 mRNA were detected in the rectus abdominus muscle of 10 lean subjects (UCP1/cyclophilinA ratio: 24±9). The PCR-amplified fragment was sequenced and found to be 100% identical to human UCP1. The UCP1 mRNA level in adult human muscle was 75-fold lower than that in fetal muscle CD34+ cells in culture.

Figure 5:
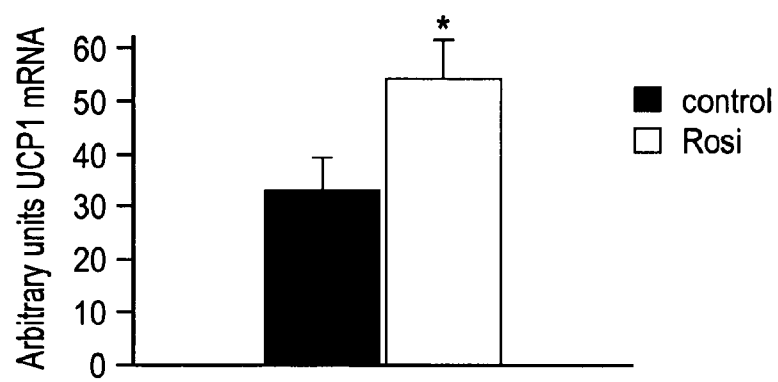
FIG. 5 shows effects of rosiglitazone on UCP1 mRNA expression in human skeletal muscle.

Since the PPARγ agonist rosiglitazone was a strong inducer of UCP1 mRNA expression in muscle CD34+ cells in culture, the effect of this compound in vivo in humans was investigated. Vastus lateralis muscle biopsies from 7 obese patients with type 2 diabetes mellitus treated for the management of their metabolic syndrome with rosiglitazone were used. The biopsies were obtained before and after 8 weeks of treatment with rosiglitazone (2×4 mg per day). The treatment with rosiglitazone resulted in a significant improvement of the patients' insulin resistance and diabetes. In that study rosiglitazone, concomitantly with the improvement in insulin sensitivity, increased the level of expression of UCP1 in muscle by about 1.6-fold. FIG. 5 shows the quantitative RT-PCR determination of UCP1 mRNA expression. The results are the means±s.e.m. of arbitrary values normalized using the corresponding cyclophilin A values (n=7, $*p<0.05$ vs. control). Since the RT-PCR conditions used were different, the arbitrary values of this figure do not provide a direct comparison to those of FIGS. 2-4.

In FIG. 5, showing UCP1 mRNA levels in skeletal muscle biopsies from a patient group (n=7), "control" corresponds to levels before treatment, and "Rosi" corresponds to levels after treatment (8 weeks) with rosiglitazone. Being a longitudinal study the effect of rosiglitazone on UCP1 levels in each individual (comparison of individual values for the "control"-before and "Rosi"-after conditions) were determined. Starting with 25 ng cDNA (produced by reverse transcription of RNA) the threshold of detection (Ct) during real-time PCR was about 22 for UCP1 and about 18 for cyclophilin. The effect of rosiglitazone (UCP1 level at end of treatment vs. before treatment) were as follows:

Patient 1: 50% increase (to 150%, control=437, Rosi=652 arbitrary units)
Patient 2: no change (to 100%, control=444, Rosi=453 arbitrary units)
Patient 3: 80% increase (to 180%, control=378, Rosi=677 arbitrary units)
Patient 4: 180% increase (to 280%, control=260, Rosi=730 arbitrary units)
Patient 5: 8% increase (to 108%, control=553, Rosi=600 arbitrary units)
Patient 6: 310% increase (to 410%, control=135, Rosi=556 arbitrary units)
Patient 7: 10% increase (to 110%, control=128, Rosi=142 arbitrary units)

Strong effects of rosiglitazone, varying between 1.5- and 4.1-fold, were observed in 4 out 7 patients. This result suggests that rosiglitazone induced the appearance of brown adipocytes and/or enhanced the expression of the UCP1 gene in existing brown adipocytes in the skeletal muscle of the patients. This effect of the PPARγ agonist may play a key role in the therapeutic effect of this agent as an insulin-sensitizer.

Example 8: Screening of Potential Modulators of the Human UCP1 Promoter/Enhancer Region The identified and isolated CD34+ cells can be used as a tool to identify agents (compounds, proteins, biologicals, and the like) that induce the differentiation of these cells into brown adipocytes or modulate the expression of UCP.

For this purpose a large region (6 kb) of DNA upstream (in 5') of the transcription start site of the human UCP1 gene (containing the promoter/enhancer region) has been cloned into a reporter/MAR GFP (Green Fluorescent Protein) or luciferase. This construct has been used to transfect CD34+ cells, and the cells grown in multiwell plates and screened for agents that increase the fluorescence (GFP) or luminescence (luciferase) of the cells, reflecting induction of gene expression (and thus increased UCP1 expression). This allows the identification of agents that can enhance the differentiation of CD34+ cells into brown adipocytes and/or the expression of UCP1 by enhancing the transcription of the UCP1 gene and/or by enhancing the translation of the UCP1 transcript, and/or by stabilizing the UCP1 transcript or protein.

For example, a PPARγ modulator or activator like rosiglitazone can be used to promote the differentiation of CD34+ progenitor cells into brown adipocytes (FIGS. 3C and 5). Another example is the use of cAMP derivatives like, 8-bromo-cAMP and/or (4-chlorophenylthio)-cAMP (FIG. 3B) or protein kinase A (PKA) activators or phosphodiesterase inhibitors. Another example is the use of triiodothyronine (T3), other thyroid hormones, agonists or modulators of the thyroid hormone receptors TRα and/or TRβ. Another example is to use β-adrenergic agonists like isoproterenol (pan-agonist) or specific $\beta_1$-, $\beta_2$-, $\beta_3$-agonists or modulators. Another is the use of modulators of the candidate receptors revealed by gene chip studies or of target genes in the signaling pathway downstream these receptors.

Example 9: Gene Chip Studies

Gene chip studies were performed to identify molecular pathways that play a role in the differentiation of CD34+ progenitor cells into brown adipocytes and/or the induction of the expression of UCP1. CD34+ cells were isolated from human skeletal muscle biopsies, and were used in two studies: (1) cAMP study: CD34+ cells were differentiated as described in Materials (Control) plus addition of vehicle (Control 1 sample) or cAMP (cAMP sample); and (2) Rosiglitazone study: CD34+ cells were differentiated as described in Materials except that rosiglitazone was omitted from the adipogenic medium (Control 2 sample). Rosiglitazone was added only to the second sample (Rosiglitazone sample) in this study.

We have found that these compounds promote the differentiation of CD34+ cells into brown adipocytes and the expression of UCP1 (see FIGS. 3B and 3C).

Total RNA was purified from these cells, and transcriptional profiles were assessed with Illumina Human WG-6 BeadChip (Expression Analysis, Inc., Durham, N.C.). Results were analyzed with Ingenuity Pathway Analysis 7.0 (trial version). These results were used to determine what molecular pathways are involved in the differentiation of CD34+ cells into brown adipocytes, and, more importantly, what molecular targets can be used for the development of agents that promote the appearance of brown adipocytes and the expression of UCP1.

This work showed that the following actions/agents should promote brown adipocyte development: a PPARγ activator, modulator or inhibitor (e.g., rosiglitazone), a PPARα activator or modulator (e.g., GW9578), a PPARδ activator or modulator (e.g., GW501516 or GW0742), a dual PPARα and PPARδ activator or modulator, a pan-PPAR (α, β, γ) activator or modulator (e.g., GW4148), a PDE4 inhibitor (e.g., rolipram or IBMX), a PDE7 inhibitor (e.g., BMS 586353 or BRL 50481 or IBMX), a NRIP1 (RIP140) inhibitor, a PTEN inhibitor (e.g., potassium bisperoxo (bipyridine) oxovanadate or dipotassium bisperoxo (5-hydroxypyridine-2-carboxyl) oxovanadate), an al-adrenergic full or partial agonist (e.g., phenylephrine or cirazoline), an RXRα activator or modulator (e.g., LGD1069 (Targretin) or 9-cis retinoic acid), a PGC-1α activator, a PGC-1p inhibitor or activator, adiponectin or an activator of adiponectin receptor AdipoR1 and/or AdipoR2, an NOS inhibitor or activator (e.g., 2-Ethyl-2-thiopseudourea or NG-nitro-L-arginine methyl ester (L-NAME) or adenosine), a Rho kinase-ROCK inhibitor (e.g., fasudil), BDNF, a monoamine oxidase (MAO) A inhibitor and/or a MAO B inhibitor (e.g., isocarboxazid, moclobemide, selegiline), an activator of SRC, an inhibitor of EGFR (e.g., erlotinib or ZD1839-gefinitib or Argos protein), an inhibitor of FAAH (e.g., URB597), an inhibitor of MAPK 1 (e.g., PD98059), or 2 (e.g., PD98059) or 4 or 5 or 7 or 8 (e.g., PD98059), an inhibitor of CDK9 (e.g., 1,5,6,7-Tetrahydro-2-(4-pyridinyl)-4H-pyrrolo[3,2-c]pyridin-4-one hydrochloride), a TGR5 agonist (e.g., oleanolic acid), an AMPK activator (e.g., AICAR), BMP-7, an mTOR inhibitor (e.g., rapamycin), and adenylate cyclase activator (e.g., forskolin), or combinations of any of the foregoing.

Materials & Methods

All organic and inorganic chemicals of analytical or molecular biology grade were purchased from Sigma Chemical Co. (St Louis, Mich.) and Gibco BRL (New York, N.Y.).

Human Tissues

Human fetal tissues were obtained anonymously, following spontaneous, voluntary or therapeutic terminations of pregnancy, from Magee Women Hospital, University of Pittsburgh, in compliance with the Institutional Review Board protocol. Developmental age (16 to 24 weeks of gestation) was estimated by measuring foot length. Informed consent to the use of fetal tissues was obtained from the patients in all instances. Adult human discarded abdominal subcutaneous WAT, originating from 45-55 year old patients undergoing plastic surgery performed one year after gastric bypass, was kindly provided by Dr Peter Rubin (Division of Plastic Surgery, University of Pittsburgh). The adult skeletal muscle tissue used for cell sorting was obtained post mortem from 50-78 year-old donors. The adult skeletal muscle used for the first group of RT-PCR studies was obtained from the rectus abdominus during surgery for either lap banding, inguinal hernia or hysterectomy of 10 lean male and female subjects. All subjects agreed to donate muscle samples during their operations and the protocol was approved by the Medical Ethical Review Committee of Deakin University. The average ages were 45±3 years and the average body mass index was 22.2±0.8. The adult skeletal muscle used for the second group of RT-PCR studies was obtained from the vastus lateralis of 7 obese type 2 diabetic male and female patients before and after 8 weeks of treatment with rosiglitazone (2×4 mg per day). The average age was 63±4 years and the average body mass index was 29.93.8. The complete clinical profile of the patients has been described in a previous publication [18]. All subjects agreed to donate muscle samples, and the protocol was approved by the Medical Ethical Review Committee of Maastricht University.

Mice

Animals were treated in accordance with the Centre Médical Universitaire (Genéve) institutional guidelines. They were housed individually and kept on a 12 h light-dark cycle in a temperature-controlled room at 24° C. They were allowed ad libitum access to water and a standard laboratory chow. The interscapular BAT of 4- to 6-week-old male 129 Sv/ev mice were excised and their precursor cells isolated and cultured as previously described [19].

Immunohistochemistry

Fresh fetal and adult tissues were gradually frozen by immersion in isopentane cooled in liquid nitrogen. Five- to 7-μm sections were cut on a cryostat (Microm HM 505 E), fixed with 50% acetone and 50% methanol, dried for 5 min at room temperature (RT), and then washed 3 times for 5 min in phosphate-buffered saline. Non-specific binding sites were blocked with 5% goat serum for 1 hour at RT. Sections were incubated overnight at 4° C. with a CD34 mouse anti-human antibody (Serotech, 1:50), then, after rinsing, for 1 hour at RT with a secondary goat anti-mouse biotinylated antibody (DAKO, 1:1000) and for 30 min at RT with streptavidin-Cy3 (Sigma, 1:1000) or for 2 hours at RT with a conjugated CD146-Alexa 488 mouse anti-human antibody (Chemicon, 1:200). Nuclei were stained with 4',6-diamino-2-phenylindole dihydrochloride (Molecular Probes, 1:2000) for 5 min at RT. An isotype-matched negative control was performed with each immunostaining.

Flow Cytometry

The vascular cells of fetal skeletal muscle, pancreas, lung and liver as well as of adult muscle and WAT were analysed by flow cytometry. Fresh fetal or adult muscle as well as fetal pancreas, lung and liver tissues were cut into small pieces with a scalpel in Dulbecco's Modified Eagle Medium high glucose (DMEM) containing 20% fetal bovine serum (FBS), 1% penicillin-streptomycin (PS) and collagenases IA-S, II-S and IV-S (1 mg/mL), then incubated at 37° C. for 75 min (fetal tissues) or 90 min (adult tissues) with constant stirring. Final cell dissociation was achieved between ground glass slides. Cells were washed with phosphate-buffered saline and centrifuged for 5 min at 350 g. They were resuspended in DMEM, 20% FBS, filtered at 100 μm, stained with Trypan blue and counted after dead cell exclusion. The WAT stroma vascular fraction was prepared by collagenase digestion according to Champigny et al. [20]. Cells ($10^5$ for analysis and around 30·106 for sorting) were incubated with one of the following directly coupled mouse anti-human antibodies: CD45-APC Cy7 (Santa Cruz Biotechnologies, 1:200), CD56-PE Cy7 (BD Pharmigen 1:100), CD34-PE (DAKO, 1:100) and CD146-FITC (Serotec, 1:100) in 1 ml DMEM, 20% FBS, 1% penicillin-streptomycin, at 4° C. for 15 min. After washing and centrifugation cells were incubated 30 min with 7-amino-actinomycin D (7-AAD, BD Pharmigen, 1:100) for dead cell exclusion, filtered at 70 □m and run on a FACS Aria flow cytometer (Becton Dickinson). As negative controls, cell aliquots were incubated with isotype-matched mouse IgGs conjugated to APC Cy7 (BD Pharmigen, 1:100), PE Cy7 (BD Pharmigen, 1:100), PE (Chemicon, 1:100) and FITC (US Biological, 1:100) under the same conditions.

Cell Culture

Cells were seeded at $2 \cdot 10^4$ per $cm^2$ in 0.2% gelatin coated plates, cultured until confluency (4-6 days) at 37° C. in EGM2 medium (Cambrex Bio Science, Walkersville, Md.) and until differentiation (8-12 more days) in a modification of the adipogenic medium described by Rodriguez et al. [21] consisting in DMEM-Ham's F-12 medium containing 0.86 μM insulin, 10 μg/ml transferrin, 0.2 nM triiodothyronine, 1 μM rosiglitazone (GlaxoSmithKline, Research Triangle Park, N.C.), 100 μM 3-isobutyl-1-methylxanthine (IBMX), 1 μM dexamethasone and 1% penicillin-streptomycin. For cell expansion studies, confluent cells grown in EGM2 medium only were detached by treatment with trypsin-EDTA for 3-5 min at 37° C., and then split 1:3 and cultured as described above. Human white adipocytes in primary culture used in the oxymetry studies were obtained as previously described [22].

RT-PCR

Total cell RNA was prepared using the kit NucleoSpin® RNAII (Clontech, Palo Alto, Calif.) or Extract-all solution (Eurobio, Courtaboeuf, France) and quantified by Biophotometry (Biophotometer, Eppendor). Oligo-dT primed First strand cDNA were synthesized using the Superscript™ II RNase H Reverse Transcription kit (Invitrogen, Carlsbad, Calif.) and oligo-dT primers or the High Capacity cDNA Reverse Transcription kit (Applied Biosystems, Foster City, Calif.) and random primers. Quantitative real-time PCR was performed using ABI rapid thermal cycler system, and a SYBR Green PCR master mix (Applied Biosystems, Foster City, Calif.). Cyclophilin A was used as a control to account for any variations due to the efficiency of the reverse transcription. The upstream and downstream oligonucleotide primers were chosen on both sides of an intron to prevent amplification of contaminating genomic DNA.

The primers used for real time quantitative PCR in human cells and in mouse brown adipocytes are as follows:

hUCP1
Sense primer:
(SEQ ID NO: 1)
5'-CCTCACCGCAGGGAAAGAA-3'

Antisense primer:
(SEQ ID NO: 2)
5'-CTAACGACTGGAGGAGTGGCA-3'

Amplicon position: 429-504.

Accession No.: NM_021833.

mUCP1
Sense primer:
(SEQ ID NO: 3)
5'-CGATGTCCATGTACACCAAGGA-3'

Antisense primer:
(SEQ ID NO: 4)
5'-TTGTGGCTTCTITTCTGCGA-3'

Amplicon position: 996-1063.

Accession No.: NM_009463.2.

hleptin
Sense primer:
(SEQ ID NO: 5)
5'-CCAAAACCCTCATCAAGACAATT-3'

Antisense primer:
(SEQ ID NO: 6)
5'-AAGTCCACCGGTTTGGACTTCA-3

Amplicon position: 143-238.

Accession No.: BC069323.

hcyclophilin A
Sense primer:
(SEQ ID NO: 7)
5'-CATCTGCACTGCCAAGACTGA-3'

Antisense primer:
(SEQ ID NO: 8)
5'-GCAAAGTGAAAGAAGGCATGAA-3'

Amplicon position: 466-537.

Accession No.: NM_203431.

mcyclophilin A
Sense primer:
(SEQ ID NO: 9)
5'-CAAATGCTGGACCAAACACAA-3'

Antisense primer:
(SEQ ID NO: 10)
5'-CCATCCAGCCATTCAGTCTTG-3'

Amplicon position: 343-412.

Accession No.: NM_008907.

Primer used for real time quantitative PCR in human skeletamuscle are as follows:
hUCP1
Sense primer:
(SEQ ID NO: 11)
5'-TCCGGCTCCAGGTCCAA-3'

Antisense primer:
(SEQ ID NO: 12)
5'-TGATTGTTCCCAGGACACCTTT-3'

Amplicon position: 240-311.

Accession No.: NM_021833.

hcyclophilin A
Sense primer:
(SEQ ID NO: 7)
5'-CATCTGCACTGCCAAGACTGA-3'

Antisense primer:
(SEQ ID NO: 8)
5'-GCAAAGTGAAAGAAGGCATGAA-3'

Amplicon position: 466-537.

Accession No.: NM_203431.

Primers used for analytical PCR are as follows:
CD34
Sense primer:
(SEQ ID NO: 13)
5'-CATCACTGGCTATTTCCTGATG-3'

Antisense primer:
(SEQ ID NO: 14)
5'-AGCCGAATGTGTAAAGGACAG-3'

Amplicon position: 1172-1591.

Accession No.: M81104.

CD56
Sense primer:
(SEQ ID NO: 15)
5'-GTATTTGCCTATCCCAGTGCC-3'

Antisense primer:
(SEQ ID NO: 16)
5'-CATACTTCTTCACCCACTGCTC-3'

Amplicon position: 542-873.

Accession No.: BC014205.

CD45
Sense primer:
(SEQ ID NO: 17)
5'-CATGTACTGCTCCTGATAAGAC-3'

Antisense primer:
(SEQ ID NO: 18)
5'-GCCTACACTTGACATGCATAC-3'

Amplicon position: 940-1579.

Accession No.: Y00638.

CD146
Sense primer:
(SEQ ID NO: 19)
5'-AAGGCAACCTCAGCCATGTCG-3'

Antisense primer:
(SEQ ID NO: 20)
5'-CTCGACTCCACAGTCTGGGAC-3'

Amplicon position: 168-603.

Accession No.: M28882.

β-actin
Sense primer:
(SEQ ID NO: 21)
5-CCTCGCCTTTGCCGATCC-3'

Antisense primer:
(SEQ ID NO: 22)
5'-GGAATCCTTCTGACCCATGC-3'

Amplicon position: 25-229.

Accession No.: NM_001101.

Arbitrary units were determined by normalizing target mRNA levels to cyclophilin mRNA levels (based on Cts), wherein the cyclophilin levels were first divided by 100,000 for ease of reference. For example, a ratio of target mRNA to cyclophilin mRNA of 0.01797 is expressed as 1797.

Validation of the Human UCP1 Amplicon

The PCR-amplified fragment was cloned into the pCR2.1-TOPO vector through the TOPO-TA cloning system (Invitrogen, Carlsbad, Calif.) and purification of color-selected colonies was performed using the Qiaprep Spin Miniprep (Qiagen, Hilden, Germany). Sequences were determined with oligonucleotide M13 Reverse on the pCR2.1-TOPO vector using the Applied Biosystem Big Dye sequencing kit on an ABI 3700 automated sequencer (Applied Biosystems, Foster City, Calif.).

Western Blots

Cultured cells were collected with a rubber policeman in 200 µl of RIPA buffer (150 mM NaCl, 1% Nonidet P-40, 0.5% Na deoxycholate, 0.1% SDS, 1:200 protease inhibitor cocktail (Sigma Chemical Co, St Louis, Mich.) and 50 mM Tris/HCl pH 8.0). Human BAT and skeletal muscle were homogenized in the above RIPA buffer. The protein content was determined according to the technique of Lowry [23]. Western blots were performed as previously described [24]. The UCP1 protein was detected using a 1/500 diluted rabbit anti-mouse UCP1 polyclonal primary antibody generously provided by Dr B. Cannon (Stockholm, Sweden). This antibody had been raised against the C-terminal decapeptide of mouse UCP1, that shares 80% identity with human UCP1 and 0 and 10% identities with human UCP2 and UCP3, respectively. Glyceraldehyde phosphate dehydrogenase (GAPDH) protein was detected using a 1/5000 diluted mouse anti-mouse GAPDH monoclonal primary antibody (Chemicon International, Inc, Temecula, Calif.). 1/5000 diluted goat anti-rabbit or anti-mouse peroxidase-labelled secondary antibodies (Sigma-Aldrich, St. Louis, Mo. or Bio-Rad, Hercules, Calif.) were used. A SeeBlue® Plus 2 Pre-stained Standard Ladder (Invitrogen, Carlsbad, Calif.) was used. Protein signals were detected by chemiluminescence using a standard ECL kit and developed on a Hyperfilm ECL film.

High-Resolution $O_2$ Consumption Measurement

Oxygen consumption was measured using a 2-injection chambers respirometer equipped with a Peltier thermostat, Clark-type electrodes, and integrated electromagnetic stirrers (Oroboros® Oxygraph, Oroboros, Innsbruck, Austria). Measurements were performed at 37° C. with continuous stirring in 2 ml of DMEM F12, 10% new born calf serum. Under these conditions, the serum provided the fatty acids necessary to sustain UCP1 uncoupling activity. Before each 02 consumption measurement, the medium in the chambers was equilibrated with air for 30 min, and freshly trypsinized cells were transferred into the respirometer glass chambers. After observing steady-state respiratory flux, ATP synthase was inhibited with oligomycin (0.25-0.5 mg/I) and cells were titrated with the uncoupler carbonyl cyanide 3-chlorophenylhydrazone up to optimum concentrations in the range of 1-2 µM. The respiratory chain was inhibited by antimycin A (1 µg/ml). Oxygen consumption was calculated using DataGraph software (Oroboros software).

Gene Chip Analysis

The total RNA of fetal muscle CD34+ cells expanded in culture for up to 3 passages (4 weeks) and of human muscle biopsies were prepared as described above. The quality assurance measurements, the preparation of the cRNA targets and the gene chip analyses using Illumina Human WG-6 BeadChip were performed by Expression Analysis, Inc. (Durham, N.C.). BeadStudio nonparametric methods were used for the computation of Detection P-Values.

Statistical Analysis

Data are expressed as means±s.e.m. Significances were evaluated using the unpaired Student's t-test. A paired Student's t-test was used to determine the effects of rosiglitazone on human skeletal muscle UCP1 mRNA levels. Significances were set at p<0.05.

Cloning of the Human UCP1 Promoter/Enhancer Region:

To develop our screening strategy, the human UCP1 promoter/enhancer was subcloned as follow:

A human BAC (bacterial artificial chromosome) clone #RP11-5K16, (AC 108019) containing the human UCP1 (uncoupling protein-1) promoter/enhancer region, was obtained from the CHORI (Children's Hospital Oakland Research Institute) BAC-PAC resources service. The selected promoter/enhancer region starts at position −25 upstream of the 5'UTR (UnTranslated Region) of the human UCP1 gene (accession number: NM_021833). Based on the human UCP1 gene initiation codon, the full cloned promoter/enhancer sequence locates between position −149 and −6269.

Primer sets were designed to amplify either:
i) the full targeted promoter/enhancer region (6120 bp starting at position −25 upstream of the UCP1 5'UTR), Left primer:
(SEQ ID NO: 23)
5'-TCGTAAGCTTAGAGGCGGCGGCTGCAGACGGAGCGCGGTGTT-3'

Right primer:
(SEQ ID NO: 24)
5'-ACGAAGATCTCATTACCCCAAATAGCATCACA-3' ii) the proximal targeted promoter/enhancer region (3685 bp upstream of the −25 nucleotide of the UCP1 5'UTR)

Left primer:
(SEQ ID NO: 25)
5'-TCGTAAGCTTAGAGGCGGCGGCTGCAGACGGAGCGCGGTGTT-3'

Right primer:
(SEQ ID NO: 26)
5'-ACGAACCGGTCAGAAGTGGTGAAGCCAGCCTGC-3' iii) the distal targeted promoter/enhancer region (2435 bp upstream of the proximal targeted promoter/enhancer region) as indicated:

Left primer:
(SEQ ID NO: 27)
5'-TCGTACCGGTACAGGCTCTGGGAAGTAGGAGAAAGT-3'

Right primer:
(SEQ ID NO: 28)
5'-ACGAAGATCTCATTACCCCAAATAGCATCACA-3'

Each primer contains a restriction site to facilitate subsequent cloning in mammalian expression vector (see below).

Cloning of the promoter/enhancer in PCR reaction was performed with 500 ng of BAC #RP11-5K16 as template, using Takara Ex Taq DNA Polymerase kit (Clontech) for amplification. PCR program steps were as follow: Initialization step, 92° C. for 2', followed by 28 cycles: denaturation: 92° C.-30 seconds/annealing: 59° C.-40 seconds/extension: 68° C.-5 minutes 30 second, with a final elongation step 68° C.-8 minutes.

The full promoter/enhancer, proximal or distal promoter/enhancer were subsequently subcloned in the reporter/MAR element-containing vector p1-68_GFP at the BlgII/HindIII sites, replacing the SV40 promoter cassette [25]. Alternatively, the luciferase-based pGL3 Basic vector (Promega) was also used as another reporter type, using the same BgIII/NcoI sites for subcloning purpose.

The human UCP1 promoter sequence cloned was confirmed by state-of-the-art sequencing, performed at biotechnology company, Fasteris SA, Switzerland. The sequence of the human UCP1 promoter sequence is provided as follows (SEQ ID NO. 29):

5'-CATTACCCCAAATAGCATCACATTCTATCTCTGGATCACCATTTT

TACACTTATCTAGAATTTGCCCACCTGTAGTTTCCACTCTTCGGCACT

AATTATTTTGCTTAATTGCGTACAGAACAAATCTACCCCGTCCACTGT

CTATGCCTTCAAGTATCTGAGAACAGTAATGTCCTGTTCGGTAAGTCA

TTTTCTCCTTTTCACTCTCTGGTCCTTCCATGGGCTTCAATCCCCAT

ACACCTCTTTTTTCTAAATTTCATAGGTCAGTTTTCCTGTCTCTTCTA

CCAGGTTCTACTGAAGATGAAAAAAAGTGCTTTTTTAAACCAAAGTA

TTGCAATGTTTATTTTATCTTTGTAAGTTCCTTAGTAATATATACAAA

TCAAGTAAAAGATATATGTTGCATGTGATATTTTAACTTTTGATATGA

CTTATTGAAAAAATATATAAGGATACATAGCCATTGTGTGTCTTCAAA

TCATAGGAAAGTATCATGTCGCGAATGTATTGGGAAGGCAGTTGGGGT

ATCACGTAGTAGTTGAGAGTTAGGGGGTCAGGCAGATCCTCAGTGTAC

CATTTACTGGTTCCGTGACCTAGGAGAAGTTATTTAACTTCTCTGAGC

TCTCTGAGTTTCCTCATCAGTGAAGGGGAATAACAATAATATATGCCT

CCAAAGGCCGCAATGAGGACTAACTGTGTTAAGTTTTGTAAAATGCCT

AAAATATTATAGTGTCTGGCACTTGTTCAATGCTATGTATTTGTTAAA

TACATGACATGAATAAATCTTTCATTGAGTTATGAGGATTAGGTACAT

CAGGTGCTTAGCATAAAGAGTGATTTATTAATAAGAATAGGCTCATGA

TGCAGGAATATTCATCACATATGTAAATAATCTGAAGCTCAGAGAAGT

TAAGTAATTTGGCCATGCTTACCCAGTCAGTTATTATCTTAGTGAGAA

TTTGAACATGGGCCTCCTGGTCTCTTAATCACCATGCTATACCACTTA

TATCAGCATAGAAATGGAATATTTTCTCCTTAACGCAGAGTTTGATAG

TCTTTGTCTCTTTGTATTGGGCTGGACTAAGAAAACCCAATCCTGTCC

TCTTTCTACTTTTTCTCTGTTCCTAAGAGCACTCCCCTTTCTCTGTTG

TATATCAGTTCCTAATGGTAGACACTTGAGCACCACTATTCTGTACAG

CTCTCCGACAATCCCACATCTAGATGCCAAGCTGAGGTTGGCATTCTC

ACTAATTTGCTGTTATAAATATTAAGCTATCATAAGCGTTAGCCTACA

TATGACTCTTTCATATGTTAGTTAATTATTTTAGGGTAGAAATCCAAA

AGTGGAGTTACCAGAAGTGGATATAGACATTCTGGCTGGGTGTGATGG

TTCATGCCTGTAATCCCAGCACTTTGGGAGGCAGAGGCAGGCGGATCA

CTTGAGGCCAGGAGTTTGAGATCAGCCTGGGCAACACAGCGAAACCC

CATCTCTACTAAAAATTCCAAAACTAGCCAGGCATAGTGGCACATGCC

TGTACTCCCAGCTACTTGGGAGGCTAAGACACAAGAATCGCTTGAACC

CGGGAGGGAGGTGGAGGTTGCGGTGAGCTGAGATTGTGCCACCGTACT

CCAGCCTGGGTGACACAGCTAGACTCTGTTTCAAAAAAAAAAGAAAA

AGAAAAGAAAAAAATAGACTTTCTCTTGGCTCAGTGTATACTGCCAAA

TTGTTTTCCAAAAAAATTGTGTCAATGTATAACACCATCACTAATATA

GTATTGATATTATGGTTATTACATTTTAAAATTCATAATTTGTAATTA

TAACATTCATAATTTATTACTATTTATAATATTAATGTAAATGTATAT

TATATATAAATGTTATAGTAATTATAACTTTGGTAGTGACAAAGTATT

AATTTATTAGGTGAAGTATATGCTTTTTTATTAGTGATAATAAATATA

TCCTCTCTCCCATTATAAAAGTTTGTATTTCTTCTTTTAGAAATTGAT

TCTTCTGTCATTTGCACATTTATCTGTATAATTATAACAGGGTATTTC

CCAGTGGTGGCTAATGAGAGAATTATGGGAAAGTATAGAACACTATTC

AAATGCAAAGCACTGTATGATTTTTATTTAATAGGAAGACATTTTGTG

CAGCGATTTCTGATTGACCACAGTTTGATCAAGTGCATTTGTTAATGT

GTTCTACATTTTCAAAAAGGAAAGGAGAATTTGTTACATTCAGAACTT

GCTGCCACTCCTTTGCTACGTCATAAAGGGTCAGTTGCCCTTGCTCAT

ACTGACCTATTCTTTACCTCTCTGCTTCTTCTTTGTGCCAGAAGAGTA

GAAATCTGACCCTTTGGGGATACCACCCTCTCCCCTACTGCTCTCTCC

AACCTGAGGCAAACTTTCTCCTACTTCCCAGAGCCTGTCAGAAGTGGT

GAAGCCAGCCTGCTCCTTGGAATCCAGAACTACTTTCAGAATCTTGAA

CTTCTGTGACCTCTCAGGGTCCCCTTGTGTGAAGTTTTTGACGTCAGC

TTCTCCTGTGACCCTTAGAAGTCACTCTTGTGTCTAGCACATCCCAGG

TGCTCAGTCACCATTGAACTACAGTCATACTATCTCCTGGCAAAGGCT

CTTAACTGTCCATGTTAGCCTGATATTAATATCCTGGAAGCTTATACT

GTCGTTCTTCCTTCCAGGTTTAAATAAGGCAGCCCCTTTATCCTGTCA

CAGGTCCTCTCTCCCTACCTATCCTTACCTGTTTTGGATAACAACCTT

TCTTCATTTCTAATAGATTTATTTATTTCTCACATTTCCTTCCCTTAT

CATAGTTTTCCTCTCACTTTCTCCTCTAGTTTGTCATACTCTGGCTTT

AAAACATGCAAACATGTGCCTTATGGGGAAAAAAAGACAATTTTAATT

TACCTTGCTTCTTTACAAATGTATTGTGGCTTCTTCTTATAGTCCAAA

TCTAAAACTCTTTACCCACCCACTGCCTTGAACTCCTTCCTCGTTGTG

AAAGTAGGATGGGCAAAGAGAGAATGCATGCCCCTCCCAACTGCTCA

AACAAGTAAAGGTGCTGTTACAGTTATCTTTTGCTACCTTAATACAAT

AATTATTTTATTATATCTCACAATTTTATGGATCAGGAATTTAGACTG

GGCTCAGCTAGGCGATTCTTCTGCTTTACTGACATCATAGGAGATCAC

TTGGTGGTATTCAACTGTCAGGTAGGCTTATCTGGAGGGTCCAAGATA

GCTGTACTCTGGTGCCTGGTGCCTTGGTAAAGAGGGATGATGATGTGG

GGCCTCTCCAGCATGAACAGCCTCAGAGAAGTTTGCTTTCTTACATGC

TGGCCCAGGGCTCCAAGAGCAAATGTTGCAGTGAGTAAAGCAGAAGAT

ACAAGGACTTTTATAATCTGGTCTCAGAAGCCACATGGCATCAGTTCT

GTATTATTCTATTGGTCAAAACATTCATAAGCCTGCCAGATGCAAGGG

GAAGGCATATGTACCCTCATCTTTTGATGGGAGGAATGTGATGGATTT

```
GCAATTATGTTTTAAAACTACTACAGACAGAACCACTGAGAAAGATTC

ATGGGTAGCTTTGGGGTGAGGACTGGGAATTAACCTGTTGATAGCAGA

GGTTCACTAGAGTCAACAAGGAATAAGGTCTCCTCTTGTACACTTTAG

TCATACTATACCAACATTCTTAACCACTGCTTAGCCATCAGCCTCACA

ACATAACAACTCCATCATAGTTGTACTCCCTAAGATCACCAACAATGT

TAGAGTCAAATCCGGTAGGTTTTTCTTTGTTTTTGTCCTCCTGACATT

TTTTCTAAACTTGACACTGGTCAGACCCAATCTTTCTTTAATCATATT

CTTAAATACCAGTTCTATCACTGGATATGTTACTGTTTCTTGTTCTCA

CTCTACCTTTGACAAAGCCATTCTTTCCAGACTATAACTCTGGGTCTG

GGTCCCCCTATGGTTTGGCCCTTGAATTCTTTTCCTAGTCCTATTTGA

CTAGCCCCATTTTCCCGTGAAAAGCATGCCCCTTTCATTGCATCCATA

TCATGACTACCAAATACCTCCTCTATTTCTTCCTCTTTTAGCATGTTA

AATGCAGCTTCCTAAGCTCTCTATCTGGATATCAACAGTATTCTCTCC

AAATAATTCTAAGACTTTAAAAATTGGTTTAATCTTCTTACCCCTAAA

ATCACCCCCCTTACCAACTGCCTCATGACAATCATTGGTACTGTCACT

GAGCTTGCAACCCATGTTCTTAAACATAGAGTAATCTTTGACTCCACA

TCTAATCATTCATAAAGCTGTATTGTCTATCAAATTAAATCTGACATT

TATGTGAGAGCACTTCATAGTCTGTAAAGCACTACACAGGTGATAACA

TGAAGCTACACTCATAATGGATTTGCAGGCTCTGCTTCTCATTTGGCT

TCTACAGCCTCATCCCTCACCAACTTCTTGCCCTACCTCTCTCTTTCT

TCCCCATCACCCAATTTCCCAGTCAGTCAGGCCAACAGAATGCATTCT

ATATACGCGACTTGCTTTCCCCAACATCTTTGCCTGTATGCATGCCAC

TTATTTGCCTCAGTTGATCTTTATTTCAACAAGTGTTTGCAGAGGAGA

AACCTCGCTGGCTCCTTCTCCTTTCTATTTTTTTCAGAGGCTACCCG

TCAGGTCAACATTGCCTTTTTCAGGGAAGCTCTGCAAGCCTGACCTCC

CTTGGAAGTGCCTTAGGACTGGCTTCTTGCACAGTACACAACCTTTAC

TTATAGAGGGTTTGGAGATTATTCTTTATTCATGTCTTATTTCTCCTG

CTCCTGGAGGAGATGACTCTGACTTCCACTGACTCTTTTGGGGGCTT

AAGTCAGGGTTGAGTACCAGAGGCCCTAAATAGCTGGACGTGGATTCT

GGTAATATCAAATCCATCTTTGGCTTAACTGAGAGGTTCTGAAAGCTG

GGACCTGACCTTGTCCATTTCCCTCTTTCTCCAGTTTCCTATTATTTC

CCACTGTTTTTTTTAAAAGTTTTTTGTTTTCTTAAGTTTTCACAAGAA

TAAACATTGAAAATAAAATTTGCACAAAGATCGAACTAGGAAAGGCCA

CACAACCAACACATATTACATCATTATAGGTAAGTTAGCAGGGAGATT

TCAGACCTGGGCTAGCTCTGGAACCACATTTTACACTGTTGAAAATAA

AAGCTGGAGTACAGATGAGTTTCCCAGGTTCACAGAGTTGGTAAGCTG

GAGAGCTGCACCTGGAGCCAAGCAACCTGCCCTGTCCTTTCCACTGCA

CCCTCTAAGAAATCTAATTAGAAGGAACAGGTGGTATCTCATTTTGTA

CGGTGCTTTAGCAATGTACTATTTGCTTTCTAGTGTGTCTATTGTCTC

GTTTGACATCTTCTCTGAAAAAGTGATGAAACGAAACGCTCTTTTTGA

CAAGTTCAGAGTGCTCTTGGTTCCTGTGTGGGATTCTTCCAAGTCTGA

ATTTGGTAGTGGGAAGAGAAGGAATCCGGAGGAAGGAGGATGAGAAGT

TTAAAGGAGAGGAAAGGGAAGCAGAGAAGGCCGCAAGGTGCCTGCAAG

ATGTCTGGGGAGTTGGAGGAATGGAAGAGTGCCCCGCTCTTCCTTCTG

GGAGAGCTCCAGCTAGGCAGAACCTTTCACCAAGGCTCTGATATCGTG

CTGGTTTCCGAAAGCCCCAGCCGAAGGTGTGCAGCCAAAGGGTGACAG

AAGGTGAGGCACGTGCGGGGCGCGGGTGCTGACCGCCGCGGTGCGCC

CTCCCTCCGACGTGCGGTGTGCGGGGCGCAGACAACCAGCGGCCGGCC

CAGGGCTTTCGGGGAGCGAAGCAGGGCTCCCGAGGCACCGAGCGAGAA

TGGGAATGGGAGGGACCCGGTGCTCCCGGACACGCCCCCGGCAGGTCC

CACGCCCGGGTCTTCTGAGACCTCGCGCGGCCCAGCCCGGGAGCGGCC

CAGCTATATAAGTCCCAGCGGAAGACCGGAACGCAGAGGGTCCTGCTG

GCGCGAGGGTGGGTAGGAGGGGACGCGGGGACTCGGCCCCCAACACCG

CGCTCCGTCTGCAGCCGCCGCCTCT-3'
```

The section headings and subheadings used in this specification are for organizational purposes only and are not to be construed as limiting the subject matter described in any way. Further, while the present teachings are described in conjunction with various embodiments, it is not intended that the present teachings be limited to such embodiments. On the contrary, the present teachings encompass various alternatives, modifications, and equivalents as will be appreciated by those of skill in the art.

REFERENCES

[1] M. Klingenspor, Cold-induced recruitment of brown adipose tissue thermogenesis, Exp Physiol. 88 (2003) 141-148.

[2] B. Cannon, J. Nedergaard, The biochemistry of an inefficient tissue: brown adipose tissue, Essays Biochem. 20 (1985) 110-164.

[3] N. J. Rothwell, M. J. Stock, A role for brown adipose tissue in diet-induced thermogenesis, Nature. 281 (1979) 31-35.

[4] B. B. Lowell, V. S-Susulic, A. Hamann, J. A. Lawitts, J. Himms-Hagen, B. B. Boyer, L. P. Kozak, J. S. Flier, Development of obesity in transgenic mice after genetic ablation of brown adipose tissue, Nature 366 (1993) 740-742.

[5] H. M. Feldmann, V. Golozoubova, B. C. M. Cannon, J. Nedergaard, UCP1 ablation induces obesity and abolishes diet-induced thermogenesis in mice exempt from thermal stress by living at thermoneutrality, Cell Metab. 9 (2009) 203-209.

[6] J. Kopecky, G. Clarke, S. Enerbäck, B. Spiegelman, L. P. Kozak, Expression of the mitochondrial uncoupling protein gene from the aP2 gene promoter prevents genetic obesity, J Clin Invest. 96 (1995).

[7] K. Tsukiyama-Kohara, F. Poulin, M. Kohara, C. T. DeMaria, A. Cheng, Z. Wu, A. C. Gingras, A. Katsume, M. Elchebly, B. M. Spiegelman, M. E. Harper, M. L. Tremblay, N. Sonenberg, Adipose tissue reduction in mice lacking the translational inhibitor 4E-BP1, Nature Medicine 7 (2001) 1128-1132.

[8] K. Almind, M. Manieri, W. I. Sivitz, S. Cinti, C. R. Kahn, Ectopic brown adipose tissue in muscle provides a mecha-

[9] M. Del Mar Gonzalez-Barroso, D. Ricquier, A. M. Cassard-Doulcier, The human uncoupling protein-1 gene (UCP1): present status and perspectives in obesity research, Obes Rev. 1 (2000) 61-72.

[10] B. Cannon, J. Nedergaard, Brown adipose tissue: function and physiological significance, Physiol Rev. 84 (2004) 277-359.

[11] W. D. van Marken Lichtenbelt, J. W. Vanhommerig, N. M. Smulders, J. M. Drossaerts, G. J. Kemerink, N. D. Bouvy, P. Schrauwen, G. J. Teule, Cold-activated brown adipose tissue in healthy men, N Engl J. Med. 360 (2009) 1500-1508.

[12] A. M. Cypess, S. Lehman, G. Williams, I. Tal, D. Rodman, A. B. Goldfine, F. C. Kuo, E. L. Palmer, Y. H. Tseng, A. Doria, G. M. Kolodny, C. R. Kahn, Identification and importance of brown adipose tissue in adult humans, N Engl J. Med. 360 (2009) 1509-1517.

[13] K. A. Virtanen, M. E., J. Orava, M. Heglind, R. Westergren, T. Niemi, M. Taittonen, J. Laine, N. J. Savisto, S. Enerbäck, P. Nuutila, Functional brown adipose tissue in healthy adults, N Engl J. Med. 360 (2009) 1518-1525.

[14] H. L. Garstka, W. E. Schmitt, J. Schultz, B. Sogl, B. Silakowski, A. Perez-Martos, J. Montoya, R. J. Wiesner, Import of mitochondrial transcription factor A (TFAM) into rat liver mitochondria stimulates transcription of mitochondrial DNA, Nucleic Acids Res. 31 (2003) 5039-5047.

[15] Z. Wu, P. Puigserver, B. M. Spiegelman, Transcriptional activation of adipogenesis, Curr Opin Cell Biol. 11 (1999) 689-694.

[16] Z. Zhou, T. S. Yon, Z. Chen, K. Guo, C. P. Ng, S. Ponniah, S. C. Lin, W. Hong, P. Li, Cidea-deficient mice have lean phenotype and are resistant to obesity, Nat. Genet. 35 (2003) 49-56.

[17] L. A. Foellmi-Adams, B. M. Wyse, D. Herron, J. Nedergaard, R. F. Kletzien, Induction of uncoupling protein in brown adipose tissue. Synergy between norepinephrine and pioglitazone, an insulin-sensitizing agent, Biochem Pharmacol. 52 (1996) 693-701.

[18] M. Mensink, M. K. Hesselink, A. P. Russell, G. Schaart, J. P. Sels, P. Schrauwen, Improved skeletal muscle oxidative enzyme activity and restoration of PGC-1 alpha and PPAR beta/delta gene expression upon rosiglitazone treatment in obese patients with type 2 diabetes mellitus, Int J Obes (Lond). 31 (2007) 1302-1310.

[19] L. Lehr, K. Canola, C. Asensio, M. Jimenez, F. Kuehne, J. P. Giacobino, P. Muzzin, The control of UCP1 is dissociated from that of PGC-1 alpha or of mitochondriogenesis as revealed by a study using beta-less mouse brown adipocytes in culture, FEBS Lett. 580 (2006) 4661-4666.

[20] O. Champigny, B. R. Holloway, D. Ricquier, Regulation of UCP gene expression in brown adipocytes differentiated in primary culture. Effects of a new beta-adrenoceptor agonist, Mol Cell Endocrinol. 86 (1992) 73-82.

[21] A. M. Rodriguez, C. Elabd, F. Delteil, J. Astier, C. Vernochet, P. Saint-Marc, J. Guesnet, A. Guezennec, E. Z. Amri, C. Dani, G. Ailhaud, Adipocyte differentiation of multipotent cells established from human adipose tissue, Biochem Biophys Res Commun. 315 (2004) 255-263.

[22] J. Corre, V. Planat-Benard, J. X. Corberand, L. Penicaud, L. Casteilla, P. Laharrague, Human bone marrow adipocytes support complete myeloid and lymphoid differentiation from human CD34 cells, Br J. Haematol. 227 (2004) 344-347.

[23] O. H. Lowry, N. J. Rosebrough, A. L. Farr, R. J. Randall, Protein measurement with the Folin phenol reagent, J Biol. Chem. 193 (1951) 265-275.

[24] M. Jimenez, C. Yvon, L. Lehr, B. Leger, P. Keller, A. Russell, F. Kuhne, P. Flandin, J. P. Giacobino, P. Muzzin, Expression of uncoupling protein-3 in subsarcolemmal and intermyofibrillar mitochondria of various mouse muscle types and its modulation by fasting, Eur J. Biochem. 269 (2002) 2878-2884.

[25] P. A. Girod, D. Q. Nguyen, D. Calabrese, S. Puttini, M. Grandjean, D. Martinet, A. Regamey, D. Saugy, J. S. Beckmann, P. Bucher, N. Mermod, Genome-wide prediction of matrix attachment regions that increase gene expression in mammalian cells, Nat. Methods. 4 (2007) 747-773.

The invention claimed is:

1. A method for inducing differentiation of brown adipose tissue (BAT) progenitor cells into brown adipocytes comprising:
   providing a BAT progenitor cell isolated from skeletal muscle; and
   exposing the BAT progenitor cell to a differentiation agent in vitro, said differentiation agent comprising one or more of the following: a peroxisome-proliferator-activated receptor γ (PPARγ) activator, a peroxisome-proliferator-activated receptor α (PPARα) activator, a peroxisome-proliferator-activated receptor δ (PPARδ) activator, a dual PPARα and PPARδ activator, or a pan-PPAR (α, δ, γ) activator;
   wherein the differentiation agent induces the BAT progenitor cell to differentiate into a brown adipocyte.

2. The method of claim 1, wherein the differentiation agent comprises a peroxisome-proliferator-activated receptor γ (PPARγ) activator.

3. The method of claim 1, wherein the differentiation agent comprises rosiglitazone.

4. The method of claim 1, wherein the brown adipocyte is characterized by one or more of the following: expression of uncoupling protein-1 (UCP1) or mRNA, expression of mitochondrial transcription factor A (mtTFA) protein or mRNA, expression of PGC-1α protein or mRNA, uncoupled respiration, metabolic rate, glucose utilization rate, fatty acid oxidation rate, and a combination of any of the foregoing.

5. The method of claim 4, wherein the brown adipocyte contains UCP1 mRNA at a level higher than that of in vivo brown adipocytes in human skeletal muscle.

6. The method of claim 1, wherein the BAT progenitor cell is CD34 positive.

7. The method of claim 6, wherein the BAT progenitor cell is CD45 negative.

8. The method of claim 6, wherein the BAT progenitor cell is CD56 negative.

9. The method of claim 6, wherein the BAT progenitor cell is CD146 negative.

10. The method of claim 6, wherein the BAT progenitor cell is in primary culture.

11. The method of claim 6, wherein the BAT progenitor cell is expanded in culture for one or more passages.

12. The method of claim 1, wherein the differentiation agent comprises a peroxisome-proliferator-activated receptor α (PPARα) activator.

13. The method of claim 1, wherein the differentiation agent comprises a peroxisome-proliferator-activated receptor δ (PPARδ) activator.

14. The method of claim 1, wherein the differentiation agent comprises a dual PPARα and PPARδ activator.

15. The method of claim 1, wherein the differentiation agent comprises a pan-PPAR (α, δ, γ) activator.

* * * * *